United States Patent
Janardhanan et al.

(10) Patent No.: US 11,896,848 B2
(45) Date of Patent: Feb. 13, 2024

(54) METHODS FOR SETUP CORRECTIONS IN RADIATION THERAPY

(71) Applicant: RefleXion Medical, Inc., Hayward, CA (US)

(72) Inventors: Jayakrishnan Janardhanan, Union City, CA (US); Michael Kirk Owens, San Francisco, CA (US)

(73) Assignee: RefleXion Medical, Inc., Hayward, CA (US)

( * ) Notice: Subject to any disclaimer, the term of this patent is extended or adjusted under 35 U.S.C. 154(b) by 372 days.

(21) Appl. No.: 17/375,586

(22) Filed: Jul. 14, 2021

(65) Prior Publication Data

US 2021/0339047 A1 Nov. 4, 2021

Related U.S. Application Data

(63) Continuation of application No. PCT/US2020/013927, filed on Jan. 16, 2020.

(Continued)

(51) Int. Cl.
*A61N 5/10* (2006.01)

(52) U.S. Cl.
CPC ............ *A61N 5/1049* (2013.01); *A61N 5/103* (2013.01); *A61N 5/107* (2013.01); *A61N 5/1031* (2013.01);

(Continued)

(58) Field of Classification Search
CPC ........ A61N 5/10; A61N 5/103; A61N 5/1039; A61N 5/1042; A61N 5/1045;

(Continued)

(56) References Cited

U.S. PATENT DOCUMENTS

| 3,794,840 A | 2/1974 | Scott |
| 5,647,663 A | 7/1997 | Holmes |

(Continued)

FOREIGN PATENT DOCUMENTS

| CN | 1824342 A | 8/2006 |
| CN | 101267767 A | 9/2008 |

(Continued)

OTHER PUBLICATIONS

Corrected Notice of Allowability dated Mar. 13, 2023, for U.S. Appl. No. 17/235,812, filed Apr. 20, 2021, 4 pages.

(Continued)

*Primary Examiner* — Allen C. Ho
(74) *Attorney, Agent, or Firm* — Cooley LLP

(57) ABSTRACT

Disclosed herein are methods for patient setup and registration for the irradiation of target tissue regions. A method for positioning a patient for radiation therapy may include acquiring an image of a first patient target region and a second patient target region. A first set of patient position-shift vectors may be calculated based on the acquired image and a treatment planning image of the first patient target region. A second set of patient position-shift vectors may be calculated based on the acquired image, a treatment planning image of the second patient target region, and the first set of patient position-shift vectors. The patient may be positioned according to the first set of patient position-shift vectors in a first location. The patient may be moved to a second location and positioned according to the second set of patient position-shift vectors.

18 Claims, 14 Drawing Sheets

Related U.S. Application Data

(60) Provisional application No. 62/793,288, filed on Jan. 16, 2019.

(52) U.S. Cl.
CPC ......... *A61N 5/1037* (2013.01); *A61N 5/1039* (2013.01); *A61N 5/1045* (2013.01); *A61N 5/1047* (2013.01); *A61N 5/1048* (2013.01); *A61N 5/1081* (2013.01); *A61N 5/1082* (2013.01); *A61N 2005/1052* (2013.01); *A61N 2005/1061* (2013.01); *A61N 2005/1091* (2013.01)

(58) Field of Classification Search
CPC .. A61N 5/1047; A61N 5/1048; A61N 5/1049; A61N 2005/1052; A61N 2005/1054; A61N 2005/1061; A61N 5/1064; A61N 5/1065; A61N 5/1067; A61N 5/1069; A61N 5/107; A61N 5/1077; A61N 5/1081; A61N 5/1082; A61N 5/1031
USPC .......................................................... 378/65
See application file for complete search history.

(56) References Cited

U.S. PATENT DOCUMENTS

| | | | |
|---|---|---|---|
| 6,385,286 B1 | 5/2002 | Fitchard et al. | |
| 6,438,202 B1 | 8/2002 | Olivera et al. | |
| 6,618,467 B1 | 9/2003 | Ruchala et al. | |
| 6,714,620 B2 | 3/2004 | Caflisch et al. | |
| 6,810,108 B2 | 10/2004 | Clark et al. | |
| 7,265,356 B2 | 9/2007 | Pelizzari et al. | |
| 7,280,633 B2 | 10/2007 | Cheng et al. | |
| 7,302,033 B2* | 11/2007 | Carrano | A61N 5/1049 378/41 |
| 7,302,038 B2 | 11/2007 | Mackie et al. | |
| 7,379,531 B2 | 5/2008 | Esham et al. | |
| 7,412,029 B2 | 8/2008 | Myles | |
| 7,412,280 B2 | 8/2008 | Hertel et al. | |
| 7,446,328 B2 | 11/2008 | Rigney et al. | |
| 7,469,035 B2* | 12/2008 | Keall | A61N 5/1042 378/65 |
| 7,522,779 B2* | 4/2009 | Fu | A61N 5/1049 382/167 |
| 7,623,623 B2* | 11/2009 | Raanes | A61B 6/4458 378/68 |
| 7,639,853 B2 | 12/2009 | Olivera et al. | |
| 7,839,972 B2 | 11/2010 | Ruchala et al. | |
| 7,906,770 B2* | 3/2011 | Otto | A61N 5/1047 378/65 |
| 7,945,021 B2* | 5/2011 | Shapiro | A61N 5/1048 378/65 |
| 7,983,380 B2 | 7/2011 | Guertin et al. | |
| 8,019,042 B2 | 9/2011 | Shukla et al. | |
| 8,063,376 B2 | 11/2011 | Maniawski et al. | |
| 8,086,004 B2* | 12/2011 | Kuduvalli | A61N 5/1075 382/128 |
| 8,090,074 B2 | 1/2012 | Filiberti et al. | |
| 8,107,589 B2 | 1/2012 | Sakurai et al. | |
| 8,144,962 B2 | 3/2012 | Busch et al. | |
| 8,149,991 B2 | 4/2012 | Moreau | |
| 8,269,195 B2 | 9/2012 | Rigney et al. | |
| 8,278,633 B2 | 10/2012 | Nord et al. | |
| 8,295,430 B2* | 10/2012 | Zhu | A61N 5/1049 378/65 |
| 8,331,532 B2* | 12/2012 | Nord | G21K 1/046 378/65 |
| 8,442,287 B2 | 5/2013 | Fordyce, II et al. | |
| 8,457,372 B2* | 6/2013 | Fu | A61N 5/1049 382/128 |
| 8,467,497 B2 | 6/2013 | Lu et al. | |
| 8,483,803 B2 | 7/2013 | Partain et al. | |
| 8,509,383 B2 | 8/2013 | Lu et al. | |
| 8,536,547 B2* | 9/2013 | Maurer, Jr. | A61B 6/4447 250/492.1 |
| 8,559,596 B2* | 10/2013 | Thomson | A61B 6/4071 378/65 |
| 8,588,367 B2 | 11/2013 | Busch et al. | |
| 8,605,857 B1 | 12/2013 | Renner | |
| 8,681,938 B2 | 3/2014 | Myles | |
| 8,767,917 B2 | 7/2014 | Ruchala et al. | |
| 8,816,307 B2 | 8/2014 | Kuusela et al. | |
| 8,824,630 B2* | 9/2014 | Maurer, Jr. | G16H 20/30 378/68 |
| 8,831,706 B2* | 9/2014 | Fu | A61B 6/4458 378/65 |
| 8,836,697 B2 | 9/2014 | Nord et al. | |
| 8,861,672 B2* | 10/2014 | Maltz | A61B 6/5223 378/65 |
| 8,874,187 B2* | 10/2014 | Thomson | A61B 6/5217 378/65 |
| 8,917,813 B2* | 12/2014 | Maurer, Jr. | A61N 5/1065 378/65 |
| 9,019,307 B1 | 4/2015 | Grimm | |
| 9,061,142 B2 | 6/2015 | Vilsmeier | |
| 9,155,909 B2 | 10/2015 | Ishikawa | |
| 9,437,340 B2 | 9/2016 | Echner et al. | |
| 9,498,167 B2 | 11/2016 | Mostafavi et al. | |
| 9,616,251 B2* | 4/2017 | Filiberti | A61N 5/107 |
| 9,849,308 B2* | 12/2017 | Berlinger | A61B 6/032 |
| 9,956,428 B2 | 5/2018 | Kelly | |
| 9,956,429 B2 | 5/2018 | Holmes et al. | |
| 9,974,494 B2 | 5/2018 | Mostafavi et al. | |
| 9,990,711 B2* | 6/2018 | Lugosi | G06T 17/10 |
| 10,022,559 B2 | 7/2018 | Vilsmeier | |
| 10,065,049 B2* | 9/2018 | Lugosi | G06T 19/00 |
| 10,279,196 B2* | 5/2019 | West | A61N 5/1031 |
| 10,350,436 B2 | 7/2019 | Kelly | |
| 10,449,389 B2* | 10/2019 | Ollila | A61N 5/1045 |
| 10,456,600 B2 | 10/2019 | Owens et al. | |
| 10,674,983 B2 | 6/2020 | Black | |
| 10,688,320 B2* | 6/2020 | Voronenko | A61N 5/1036 |
| 10,695,586 B2 | 6/2020 | Harper et al. | |
| 10,737,118 B2* | 8/2020 | Mostafavi | A61B 6/037 |
| 10,799,716 B2* | 10/2020 | Morgas | A61N 5/1067 |
| 10,806,368 B2* | 10/2020 | Hebert | A61N 5/107 |
| 10,835,761 B2* | 11/2020 | Bériault | A61N 5/1048 |
| 10,918,884 B2 | 2/2021 | O'Connor et al. | |
| 10,918,885 B2* | 2/2021 | Haas | A61B 6/466 |
| 11,033,757 B2 | 6/2021 | Voronenko et al. | |
| 11,083,913 B2* | 8/2021 | Lachaine | G16H 50/70 |
| 11,154,269 B2* | 10/2021 | Shea | A61B 6/5229 |
| 11,173,324 B2* | 11/2021 | Paysan | G06T 11/008 |
| 11,278,737 B2* | 3/2022 | Peltola | G06F 17/10 |
| 11,291,858 B2* | 4/2022 | MacDonald | G16H 20/40 |
| 11,358,008 B2* | 6/2022 | Voronenko | A61N 5/1081 |
| 11,369,805 B2* | 6/2022 | Maltz | A61N 5/1038 |
| 11,369,806 B2* | 6/2022 | Laurence, Jr. | A61B 34/10 |
| 11,478,662 B2* | 10/2022 | Sayeh | G16H 40/63 |
| 11,504,548 B2* | 11/2022 | Fong de los Santos | A61N 5/1031 |
| 11,504,550 B2* | 11/2022 | Maolinbay | A61B 6/4085 |
| 11,596,807 B2* | 3/2023 | Maurer | G06T 7/246 |
| 11,617,903 B2* | 4/2023 | Lamb | G01R 33/4808 600/1 |
| 11,633,626 B2 | 4/2023 | Voronenko et al. | |
| 11,648,418 B2 | 5/2023 | Owens et al. | |
| 11,684,801 B2* | 6/2023 | Schadewaldt | A61N 5/1038 600/1 |
| 2002/0137991 A1 | 9/2002 | Scarantino et al. | |
| 2004/0079899 A1 | 4/2004 | Ma | |
| 2004/0122308 A1 | 6/2004 | Ding | |
| 2005/0207531 A1 | 9/2005 | Dempsey et al. | |
| 2006/0058637 A1 | 3/2006 | Sommer | |
| 2006/0159220 A1 | 7/2006 | Heuscher | |
| 2006/0173294 A1 | 8/2006 | Ein-Gal et al. | |
| 2008/0071131 A1 | 3/2008 | Rietzel | |
| 2008/0226030 A1 | 9/2008 | Otto | |
| 2009/0116616 A1 | 5/2009 | Lu et al. | |
| 2009/0117044 A1 | 5/2009 | Hengerer et al. | |
| 2010/0054411 A1 | 3/2010 | Nord et al. | |

(56) References Cited

U.S. PATENT DOCUMENTS

| | | |
|---|---|---|
| 2010/0086183 A1 | 4/2010 | Vik et al. |
| 2010/0150309 A1 | 6/2010 | Nord et al. |
| 2011/0049377 A1 | 3/2011 | Morf et al. |
| 2011/0122997 A1 | 5/2011 | Lu et al. |
| 2011/0163238 A1 | 7/2011 | Teshigawara et al. |
| 2011/0200170 A1 | 8/2011 | Nord et al. |
| 2011/0291015 A1 | 12/2011 | Mazin |
| 2012/0053961 A1 | 3/2012 | Wang et al. |
| 2012/0230464 A1 | 9/2012 | Ling et al. |
| 2012/0250971 A1 | 10/2012 | Holmes et al. |
| 2012/0292534 A1 | 11/2012 | Geneser et al. |
| 2013/0083004 A1 | 4/2013 | Nord et al. |
| 2013/0102830 A1 | 4/2013 | Otto |
| 2013/0188856 A1 | 7/2013 | Adler, Jr. et al. |
| 2014/0005464 A1 | 1/2014 | Bharat et al. |
| 2014/0126700 A1 | 5/2014 | Gertner et al. |
| 2014/0252227 A1 | 9/2014 | Sasai et al. |
| 2014/0270053 A1 | 9/2014 | Larson |
| 2014/0275704 A1 | 9/2014 | Zhang et al. |
| 2015/0043709 A1 | 2/2015 | Shapiro et al. |
| 2015/0161338 A1 | 6/2015 | Scherrer et al. |
| 2015/0224342 A1 | 8/2015 | Baltes et al. |
| 2015/0251017 A1 | 9/2015 | De Crevoisier et al. |
| 2015/0360056 A1 | 12/2015 | Xing et al. |
| 2015/0367143 A1 | 12/2015 | Muraki et al. |
| 2016/0023019 A1 | 1/2016 | Filiberti et al. |
| 2016/0038767 A1 | 2/2016 | Wiersma et al. |
| 2016/0074541 A1 | 3/2016 | Zalutsky et al. |
| 2016/0140300 A1 | 5/2016 | Purdie et al. |
| 2016/0193480 A1 | 7/2016 | Ribbing et al. |
| 2016/0361566 A1 | 12/2016 | Larkin et al. |
| 2016/0361568 A1 | 12/2016 | Chappelow et al. |
| 2017/0014642 A1 | 1/2017 | An et al. |
| 2017/0023494 A1 | 1/2017 | Yu et al. |
| 2017/0028220 A1 | 2/2017 | Schulte et al. |
| 2017/0087385 A1 | 3/2017 | Miettinen et al. |
| 2017/0095678 A1 | 4/2017 | Oster et al. |
| 2018/0133518 A1 | 5/2018 | Harper et al. |
| 2018/0154179 A1 | 6/2018 | Ollila et al. |
| 2018/0345042 A1 | 12/2018 | Voronenko et al. |
| 2018/0369611 A1 | 12/2018 | Owens et al. |
| 2019/0001152 A1 | 1/2019 | O'Connor et al. |
| 2020/0121953 A1 | 4/2020 | Fredriksson |
| 2020/0346033 A1 | 11/2020 | MacDonald et al. |
| 2021/0236854 A1 | 8/2021 | Voronenko et al. |
| 2022/0001209 A1 | 1/2022 | Owens et al. |
| 2022/0126117 A1 | 4/2022 | Voronenko et al. |
| 2023/0356003 A1 | 11/2023 | Voronenko et al. |

FOREIGN PATENT DOCUMENTS

| | | |
|---|---|---|
| CN | 101489477 A | 7/2009 |
| CN | 101496018 A | 7/2009 |
| CN | 102068763 A | 5/2011 |
| CN | 102641561 A | 8/2012 |
| CN | 103180014 A | 6/2013 |
| CN | 103209736 A | 7/2013 |
| CN | 103845068 A | 6/2014 |
| CN | 104284697 A | 1/2015 |
| CN | 104866928 A | 8/2015 |
| CN | 104994909 A | 10/2015 |
| CN | 105658279 A | 6/2016 |
| CN | 106563211 A | 4/2017 |
| EP | 2 072 081 A1 | 6/2009 |
| EP | 1 501 604 B1 | 12/2009 |
| EP | 1 898 234 B1 | 4/2010 |
| EP | 2 904 974 A1 | 8/2015 |
| EP | 2 990 078 A1 | 3/2016 |
| EP | 2 874 702 B1 | 9/2016 |
| EP | 3 169 402 B1 | 9/2020 |
| JP | 2002-522128 A | 7/2002 |
| JP | 2005-261941 A | 9/2005 |
| JP | 2009-160308 A | 7/2009 |
| JP | 2009-538195 A | 11/2009 |
| JP | 2012-035072 A | 2/2012 |
| JP | 2012-506734 A | 3/2012 |
| JP | 2013-059576 A | 4/2013 |
| JP | 2014-023741 A | 2/2014 |
| JP | 2014-503315 A | 2/2014 |
| JP | 2016-055161 A | 4/2016 |
| JP | 2016-168077 A | 9/2016 |
| WO | WO-00/59576 A1 | 10/2000 |
| WO | WO-2007/082126 A2 | 7/2007 |
| WO | WO-2007/082126 A3 | 7/2007 |
| WO | WO-2008/011725 A1 | 1/2008 |
| WO | WO-2008/013598 | 1/2008 |
| WO | WO-2013/024380 A1 | 2/2013 |
| WO | WO-2013/054788 A1 | 4/2013 |
| WO | WO-2013/093852 A1 | 6/2013 |
| WO | WO-2015/168431 A1 | 11/2015 |
| WO | WO-2016/023786 A1 | 2/2016 |
| WO | VVO-2016/064750 A1 | 4/2016 |
| WO | WO-2017/081768 A1 | 5/2017 |
| WO | WO-2018/183748 A1 | 10/2018 |
| WO | VO-2018/237328 A1 | 12/2018 |
| WO | WO-2019/090429 A1 | 5/2019 |

OTHER PUBLICATIONS

Extended European Search Report dated Jun. 23, 2023, for EP Application No. 20 840 804.7, filed on Jul. 2, 2020, 7 pages.

Non-Final Office Action dated Jun. 29, 2023, for U.S. Appl. No. 17/479,873, filed Sep. 20, 2021, 10 pages.

Notice of Allowance dated Feb. 1, 2023, for U.S. Appl. No. 17/235,812, filed Apr. 20, 2021, 7 pages.

Notice of Allowance dated Mar. 9, 2023, for U.S. Appl. No. 16/016,272, filed Jun. 22, 2018, 8 pages.

Adaptive Radiation Therapy: ISBN:9781439816356. 2011. CRC Press. X Allen Li (Ed.): 426 pages (cover only); URL: https://www.google.com/books/edition/Adaptive_Radiation_Therapy/9hEPvAlgPfMC (accessed Aug. 31, 2021).

Akpati, H.C. et al. (2008). "Unified dosimetry index (UDI): A figure of merit for ranking treatment plans," J Appl Clin Med Phys. 9:99-108.

Alrowaili, Z.A. et al. (2015). "2D mapping of the MV photon fluence and 3D dose reconstruction in real time for quality assurance during radiotherapy treatment," J. Instrumentation IOP Science 10:P09019, 17 total pages.

ArcCHECK® & 3DVH (2016). Sun Nuclear, located at https://www.sunnuclear.com/solutions/patientqa/arccheck3dvh, retrieved on Jul. 31, 2019, 12 total pages.

Chang, J.Y. et al. (2008). "Image-guided radiation therapy for non-small cell lung cancer," J. Thorac. Oncol. 3:177-186 (Abstract Only).

Chen, Q. et al. (2016). "SU-D-201-03: During-Treatment Delivery Monitoring System for TomoTherapy," Med. Phys. 43:3334. 1 total page.

Chen, Q. (2016) "During treatment delivery monitoring system for tomotherapy," Presentation, University of Virginia Health System, 16 total pages.

Chen, X. et al. (2012). "Smoothing proximal gradient method for general structured sparse regression," The Annals of Applied Statistics 6:719-752.

Croteau, E. et al. (2016). "PET Metabolic Biomarkers for Cancer," Biomark Cancer. 8(Suppl 2):61-69.

Dieterich, S. et al. (2003). "Skin respiratory motion tracking for stereotactic radiosurgery using the CyberKnife," *Elsevier Int'l Congress Series* 1256:130-136.

ECN Magazine (2016). "Magic plate radiation detector helps improve cancer radiotherapy," located at https://www.ecnmag.com/news/2016/03/magic-plate-radiation-detector-helps-improve-cancer-radiotherapy, retrieved on Jul. 31, 2019, 5 total pages.

Extended European Search Report dated Feb. 3, 2021, for EP Application No. 18 810 297.4, filed on May 30, 2018, 4 pages.

Extended European Search Report dated Oct. 15, 2019, for European Application No. 17 764 132.1, filed on Mar. 9, 2017, 4 pages.

Extended European Search Report dated Mar. 15, 2021, for EP Application No. 18 837 615.6, filed on Jul. 26, 2018, 8 pages.

(56) References Cited

OTHER PUBLICATIONS

Extended European Search Report dated Jun. 14, 2021, for EP Application No. 18 821 003.3, filed on Jun. 22, 2018, 5 pages.
Fan, Q. et al. (2013). "Toward a Planning Scheme for Emission Guided Radiation Therapy (EGRT): FDG Based Tumor Tracking in a Metastatic Breast Cancer Patient," *Med. Phys.* 40(8): 12 pages.
Fan, Q. et al. (2012). "Emission Guided Radiation Therapy for Lung and Prostrate Cancers: A Feasibility Study on a Digital Patient," *Med. Phys.* 39(11):7140-7152.
Final Office Action dated Jul. 14, 2021, for U.S. Appl. No. 16/582,308, filed Sep. 25, 2019, 8 pages.
Final Office Action dated May 18, 2022, for U.S. Appl. No. 16/016,272, filed Jun. 22, 2018, 31 pages.
Final Office Action dated Sep. 15, 2022, for U.S. Appl. No. 16/582,308, filed Sep. 25, 2019, 10 pages.
Fredriksson (2013). "Robust optimization of radiation therapy accounting for geometric uncertainty," KTH Engin. Sciences, pp. 8-14.
Gibbons, J.P. (2004). "Dose calculation and verification for tomotherapy," 2004 ACMP Meeting, Scottsdale, AZ., 71 total pages.
Handsfield, L.L. et al. (2014). "Phantomless patient-specific TomoTherapy QA via delivery performance monitoring and a secondary Monte Carlo dose calculation," *Med. Phys.* 41:101703-1-101703-9.
Hoeben, B.A.W. et al. (2013). "Molecular PET imaging for biology-guided adaptive radiotherapy of head and neck cancer." Acta Oncologica 52:1257-1271.
Hunt, M.A. et al. (2003). "Treatment Planning Considerations using IMRT," pp. 103-121.
International Search Report dated Nov. 16, 2018, for PCT Application No. PCT/US2018/039104, filed on Jun. 22, 2018, 4 pages.
International Search Report dated Oct. 3, 2018, for PCT Application No. PCT/US2018/035188, filed on May 30, 2018, 4 pages.
International Search Report dated Oct. 3, 2018, for PCT Application No. PCT/US2018/043954, filed on Jul. 26, 2018, 3 pages.
International Search Report dated Apr. 23, 2020, for PCT Application No. PCT/US2020/013927, filed on Jan. 16, 2020, 3 pages,.
International Search Report dated Dec. 1, 2020, for PCT Application No. PCT/US2020/040774, filed on Jul. 2, 2020, 4 pages.
International Search Report dated Jun. 27, 2017, for PCT Patent Application No. PCT/US2017/021647, filed on Mar. 9, 2017, 3 pages.
Kak, A. et al. (1988). "Aliasing artifacts and noise in CT images," Principles of computerized tomographic imaging, pp. 177-201.
Kapatoes, J.M. et al. (2001). "A feasible method for clinical delivery verification and dose reconstruction in tomotherapy," *Med. Phys.* 28:528-542.
Kapatoes, J. M. (2001). "On the accuracy and effectiveness of dose reconstruction for tomotherapy," *Physics in Med. Biol.* 46:943-966.
Keall, P.J. et al. (2001). "Motion adaptive x-ray therapy: a feasibility study," *Physics in Med. Biol.* 46:1-10.
Kim et al. "18F-FDG PET/CT of Advanced Gastric Carcinoma and Association of H ER2 Expression with Standardized Uptake Value." Asia Oceania J Nucl Med Biol, 2014; 2(1): 12-18.
Kong et al. "Effect of Midtreatment PET/CT-Adapted Radiation Therapy With Concurrent Chemotherapy in Patients With Locally Advanced Non-Small-Cell Lung Cancer." JAMA Oncol. Oct. 2017; 3(10): 1358-1365. Published online Oct. 12, 2017. Prepublished online Jun. 1, 2017.
Lu, W. (2008). "Real-time motion-adaptive delivery (MAD) using binary MLC: I. Static beam (topotherapy) delivery," Phys. Med. Biol. 53:6491-6511.
Lu, W. (2009). "Real-time motion-adaptive-optimization (MAO) in tomotherapy," Phys. Med. Biol. 54:4373-4398.
Mackie, T.R. et al. (1993). "Tomotherapy: A new concept for the delivery of dynamic conformal radiotherapy," Med. Phys. 20:1709-1719.
Mazin, S.R. et al. (2010). "Emission-guided radiation therapy: Biologic targeting and adaptive treatment," Am. College of Radiology, pp. 989-990.
McMahon, R. et al. (2008). "A real-time dynamic-MLC control algorithm for delivering IMRT to targets undergoing 2D rigid motion in the beam's eye view," Med. Phys. 35:3875-3888.
Non-Final Office Action dated Dec. 6, 2019, for U.S. Appl. No. 15/993,325, filed May 30, 2018, 8 pages.
Non-Final Office Action dated Jun. 26, 2020, for U.S. Appl. No. 16/122,735, filed Sep. 5, 2018, 16 pages.
Non-Final Office Action dated Dec. 22, 2020, for U.S. Appl. No. 16/554,258, filed Aug. 28, 2019, 11 pages.
Non-Final Office Action dated Feb. 11, 2021, for U.S. Appl. No. 16/582,308, filed Sep. 25, 2019, 9 pages.
Non-Final Office Action dated Sep. 21, 2021, for U.S. Appl. No. 16/016,272, filed Jun. 22, 2018, 34 pages.
Non-Final Office Action dated Jun. 8, 2022, for U.S. Appl. No. 16/582,308, filed Sep. 25, 2019, 9 pages,.
Non-Final Office Action dated Aug. 30, 2022, for U.S. Appl. No. 17/235,812, filed Apr. 20, 2021, 8 pages.
Non-Final Office Action dated Nov. 21, 2022, for U.S. Appl. No. 16/016,272, filed Jun. 22, 2018, 27 pages.
Notice of Allowance dated Jul. 25, 2019, for U.S. Appl. No. 16/046,746, filled Jul. 26, 2018, 8 pages.
Notice of Allowance dated Aug. 15, 2019, for U.S. Appl. No. 16/046,746, filed Jul. 26, 2018, 7 pages.
Notice of Allowance dated Apr. 20, 2020, for U.S. Appl. No. 15/993,325, filed May 30, 2018, 7 pages.
Notice of Allowance dated Dec. 11, 2020, for U.S. Appl. No. 16/122,735, filed Sep. 5, 2018, 10 pages.
Olivera, G.H. et al. (2000). "Modifying a plan delivery without re-optimization to account for patient offset in tomotherapy," Proceedings of the 22$^{nd}$ Annual EMBS International Conference, Jul. 23-28, 2000, Chicago, IL, pp. 441-444.
Papanikolaou, N. et al. (2010). "MU-Tomo: Independent dose validation software for helical tomo therapy," *J. Cancer Sci. Ther.* 2:145-152.
Pyakuryal, A. et al. (2010). "A computational tool for the efficient analysis of dose-vol. histograms for radiation therapy treatment plans," J Appl. Clin. Med. Phys. 11:137-157.
Rahmim, A. et al. (2009). "Four-dimensional (4d) image reconstruction strategies in dynamic pet: beyond conventional independent frame reconstruction," Medical physics 36:3654-3670.
Reader, A.J. et al. (2007). "Advances in pet image reconstruction," PET clinics 2:173-190.
Riederer, S.J. et al. (1978). "The noise power spectrum in computed x-ray tomography," Physics in medicine and biology 23:446.
ScandiDos (2019). Delta$^4$, located at https://delta4family.com/products, retrieved on Jul. 31, 2019, 5 total pages.
Seppenwoolde, Y. et al. (2002). "Precise and real-time measurement of 3d tumor motion in lung due to breathing and heartbeat, measured during radiotherapy," International Journal of Radiation Oncology Biology Physics 53:822-834.
Thorek, D. "Positron lymphography: multimodal, high-resolution, dynamic mapping and resection of lymph nodes after X intradermal injection of 18F-FDG." J Nucl Med. Sep. 2012;53(9):1438-45.
Thorwarth, D. et al. (2010). "Physical radiotherapy treatment planning based on functional PET/CT data," Radiotherapy Oncology, pp. 317-324.
Tuncel, N. "Adaptive radiotherapy from past to future frontiers." International Journal of Radiology & Radiation Therapy 2021; 8(2):81-84.
Varian Medical Systems (2019). MOBIUS3D, Varian oncology software products, located at https://www.varian.com/oncology/products/software/mobius3d, retrieved on Jul. 31, 2019, 3 total pages.
Written Opinion of the International Searching Authority dated Nov. 16, 2018, for PCT Application No. PCT/US2018/039104, filed on Jun. 22, 2018, 6 pages.
Written Opinion of the International Searching Authority dated Oct. 3, 2018, for PCT Application No. PCT/US2018/035188, filed on May 30, 2018, 28 pages.
Written Opinion of the International Searching Authority dated Oct. 3, 2018, for PCT Application No. PCT/US2018/043954, filed on Jul. 26, 2018, 5 pages.

(56) References Cited

OTHER PUBLICATIONS

Written Opinion of the International Searching Authority dated Apr. 23, 2020, for PCT Application No. PCT/US2020/013927, filed on Jan. 16, 2020, 4 pages.
Written Opinion of the International Searching Authority dated Dec. 1, 2020, for PCT Application No. PCT/US2020/040774, filed on Jul. 2, 2020, 8 pages.
Written Opinion of the International Searching Authority dated Jun. 27, 2017, for PCT Patent Application No. PCT/US2017/021647, filed on Mar. 9, 2017, 5 pages.
Yan, D. et al. (1997). "Adaptive radiation therapy," *Physics Med. Biol.* 42:123-132.
Zhang, H. et al. (2002). Progress in the Physics of Tumor Radiation Therapy, Beijing Medical University, China Union Medical University Joint Press, p. 164 (with English translation).
Zhao, H. et al. (2015). Practical Imaging Diagnosis, University Press, Aug. 2015, p. 167 (with English translation).
Final Office Action dated Oct. 4, 2023, for U.S. Appl. No. 17/479,873, filed Sep. 20, 2021, 10 pages.
Fontenla, D.P. et al. (2008). "IMRT treatment plans: Dosimetry measurements & monitor units validation," North Shore LIJ, Presentation, 133 total pages.
Langen, K.M. et al. (2010). "QA for helical tomotherapy: Report of the AAPM task group 148," Med. Phys. 37:4817-4853.
Parodi, K. (2015). "Vision 20/20: Positron emission tomography in radiation therapy planning, delivery, and monitoring," Am. Assoc. Phys. Med. 42:7153-7168.

* cited by examiner

METHODS FOR SETUP CORRECTIONS IN RADIATION THERAPY

CROSS-REFERENCE TO RELATED APPLICATIONS

This application is a continuation of International Patent Application No. PCT/US2020/013927, filed Jan. 16, 2020, entitled "Methods for Setup Corrections in Radiation Therapy," which claims priority to and the benefit of U.S. Provisional Application No. 62/793,288, filed Jan. 16, 2019, entitled "Methods for Setup Corrections in Radiation Therapy," the entire disclosures of each of which are hereby expressly incorporated by reference for all purposes.

BACKGROUND

Radiation therapy (e.g., image guided radiation therapy or IGRT) uses planning images acquired before a treatment session to guide the application of therapeutic radiation during a radiation treatment session. The goal of a radiation therapy system is to deliver a precise dose of radiation to a target region inside a patient and avoid irradiating organs at risk. This includes generating a treatment plan based on the acquired planning images in advance of a treatment session. Since the target region may be stationary or may be in motion (e.g., due to patient breathing, body shifts, etc.), a treatment plan may account for target region motion, and the radiation therapy system may gate radiation delivery and/or track the motion of the target region during the radiation treatment session.

However, patient setup and position registration with the coordinates of a radiation therapy system can be time-consuming, particularly because the planned target region can change in size, shape, and/or location between the time of acquisition of the planning images and the treatment session. Additionally, patient setup and position registration are typically tailored for the treatment of a single target region and may not easily accommodate the treatment of multiple target regions. Thus, improved patient setup and registration methods are desirable.

SUMMARY

Disclosed herein are methods for patient setup and registration for the irradiation of target tissue regions. In some variations, the methods may be used for the irradiation of tumor regions that are located at different regions of the patient's body and/or for the irradiation of irregularly-shaped tumor regions. In some embodiments, a method for positioning a patient for radiation therapy comprises acquiring an image of a first patient target region and a second patient target region. A first set of patient position-shift vectors may be calculated based on the acquired image and a treatment planning image of the first patient target region. A second set of patient position-shift vectors may be calculated based on the acquired image, a treatment planning image of the second patient target region, and the first set of patient position-shift vectors. The patient may be positioned according to the first set of patient position-shift vectors to a first location and/or position. The patient may be positioned at a second location and positioned according to the second set of patient position-shift vectors. Positioning the patient according to the first set of patient position-shift vectors may comprise moving a radiation therapy patient platform and/or a therapeutic radiation source according to the first set of patient position-shift vectors. The patient may be positioned at a second location and adjusted according to the second set of patient position-shift vectors. Positioning the patient according to a second set of patient position-shift vectors may comprise moving a radiation therapy patient platform and/or a therapeutic radiation source according to the second set of patient position-shift vectors. The first location may be associated with a first beam station and the second location may be associated with a second beam station adjacent to the first beam station. Moving the radiation therapy patient platform may comprise moving the platform along its X-axis, and/or Y-axis, and/or Z-axis. Moving the radiation therapy patient platform may comprise adjusting the yaw and/or pitch of the platform and moving the therapeutic radiation source may comprise adjusting the roll of a gantry to which the therapeutic radiation source is coupled. The first treatment planning image and the second treatment planning image may be the same treatment planning image. The acquired image may be a PET image. The acquired image may be a CT image. In some embodiments, calculating the first and second sets of patient position-shift vectors may occur before a therapeutic radiation source is activated. In some embodiments, a first location difference may be calculated by comparing a location of the first patient target region in the acquired image with a location of the first patient target region in the first treatment planning image. A second location difference may be calculated by comparing a location of the second patient target region in the acquired image with a location of the second patient target region in the second treatment planning image. A notification may be generated if the first location difference or the second location difference exceeds a location difference threshold. The first patient target region and the second patient target region may comprise one or more tumor regions. The first patient target region may comprise a first portion of a tumor and the second patient target region may comprise a second portion of the tumor. The first and second sets of position-shift vectors may comprise distance and direction translations. The direction translations may comprise tilt angles.

DETAILED DESCRIPTION

Figure 1A:
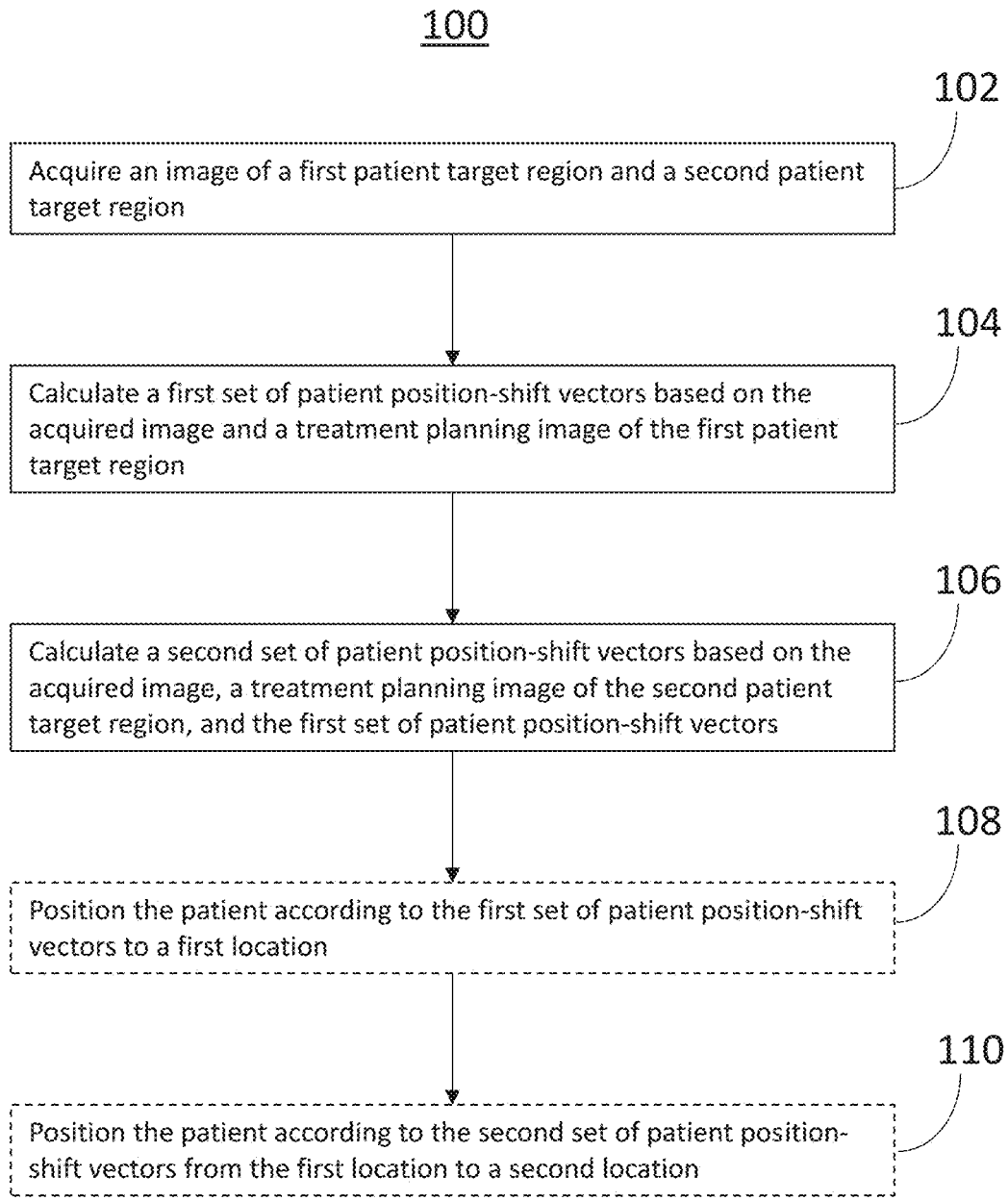
FIG. 1A is a flow chart illustrating a method of positioning a patient for radiation therapy, according to an embodiment.

Image-guided localization procedures may be used to register the location of a target region of a patient (e.g., a tumor or a portion of a tumor) or a collection of target regions relative to the location of a therapeutic radiation source. Prior to image-guided localization procedures, care providers (e.g., a doctor, clinician, or technician) may prepare a treatment plan based, at least in part, on previously acquired images of one or more target regions of the patient. Tumors, however, may take irregular and/or complex forms within a patient. Additionally, tumors may be located at different regions of the patient's body (e.g., within a patient's head and lungs). Furthermore, various factors may cause the location, shape, and/or size of a tumor to change between the time the treatment planning image is acquired and the time radiation is applied to the tumor. For example, tumors may move, grow, and/or spread within a patient over time, and tumor location relative to healthy tissue may change if a patient has lost or gained weight (e.g., due to swelling). Thus, aligning the entirety of a target region or a collection of target regions associated with one or more tumors with a radiation therapy system for an intended (i.e., future) radiation treatment session, such as when a care provider is attempting to localize a single target or multiple targets at the start of a treatment session, can be challenging.

As described herein, in some embodiments, a user (e.g., a care provider, clinician, or technician) may acquire images of one or more tumors during an image-guided localization procedure which reflect current information regarding tumor location, size, and shape prior to applying radiation. The user may compare the acquired images to treatment planning images acquired and/or prepared in advance of the procedure. The user and/or the radiation therapy system may then make adjustments to the radiation treatment session (i.e., perform setup corrections to the positioning and orientation of the patient) based on the acquired images such that the applied radiation may more effectively target the current shape, size, and location of the one or more tumors. For example, the user may define one or more regions of interest (also referred to herein as "zones" and/or "treatment fields") in an image of one or more tumors for image-guided localization. An image match or position correction may then be defined for each region of interest. In some embodiments, the radiation therapy system may automate the application of each position correction as the radiation therapy system progresses with irradiation of a target region (e.g., a tumor or a portion of a tumor) or multiple target regions. In some embodiments, the radiation therapy system may provide instructions to a user indicating position correction or adjustment instructions corresponding to position correction actions to be performed by the user (e.g., move a patient's arm or leg, or tilt and/or rotate a surface on which the patient is disposed). After the position corrections are made, the radiation therapy system may apply radiation to the real-time or updated location of a tumor or a portion of a tumor in each region of interest. Further, the tumor or tumor portions may be more accurately targeted in each region of interest by using the most effective positioning of the patient relative to the therapeutic radiation source for each region of interest, rather than keeping the patient in a position that allows for higher-quality conformal dose delivery for some tumor regions at the expense of lower-quality conformal dose delivery for other tumor regions. This may have the benefit of providing better treatment outcomes and overall conformality to treatment plans. Additionally, the time duration of radiation treatment sessions may be reduced because multiple targets may be treated during a single radiation treatment session. The reduced time may allow a care facility to treat more patients in a day. Further, the reduced time duration needed for the treatment of multiple tumors or multiple tumor portions also improves the patient experience.

In some embodiments, a method for positioning a patient for radiation therapy comprises acquiring an image of a first patient target region and a second patient target region. A first set of patient position-shift vectors may be calculated based on the acquired image and a treatment planning image of the first patient target region. A second set of patient position-shift vectors may be calculated based on the acquired image, a treatment planning image of the second patient target region, and the first set of patient position-shift vectors. The patient may be positioned according to the first set of patient position-shift vectors to a first location. The patient may be moved to a second location and positioned according to the second set of patient position-shift vectors.

FIG. 1A is a flow chart illustrating a method 100. The method 100 may be used for positioning a patient for radiation therapy. As shown in FIG. 1A, the method 100 comprises acquiring 102 an image of a first patient target region and a second patient target region. In some embodiments, the first patient target region and the second patient target region may comprise one or more tumor regions. For example, in some embodiments, the first patient target region may comprise a first portion of a tumor and the second patient target region may comprise a second portion of the tumor. In some embodiments, the first patient target region and the second patient target region may each comprise one or more discrete tumors located at different regions of the patient's body. The acquired image may be, for example, an image acquired via PET, CT, MRI, ultrasound, and/or any other suitable method. In some embodiments, for example, a CT system may be used to acquire one or more images prior to or at the start of a treatment session. In some embodiments, the CT system may be attached to the same gantry as a radiation source intended for the delivery of radiation therapy during the treatment session. In some embodiments, the CT system may be attached to a separate gantry from the gantry supporting the radiation source. In some embodiments, where radiation is delivered at discrete patient platform locations or positions (i.e., beam stations), the location of the first patient target region may be associated with the location of a first beam station of a therapeutic radiation source and the location of the second patient target region may be associated with the location of a second beam station.

A first set of patient position-shift vectors may be calculated 104 based on the acquired image and a treatment planning image of the first patient target region (also referred to herein as a "first treatment planning image"). The location of the first patient target region in the acquired image may be compared with a location of the first patient target region in the treatment planning image in 2D and/or 3D. For example, in some embodiments, a patient target region may be divided into sub-regions (e.g., sub-volumes) that may be represented by voxels, and the coordinates of each voxel of the acquired image may be compared with the coordinates of a corresponding voxel of the patient target region in the treatment planning image. Each of the vectors of the first set of patient position-shift vectors may represent the distance and directional difference between a coordinate of a voxel of the acquired image and a coordinate of a corresponding voxel of the treatment planning image. In some embodiments, the directional difference may include tilt angles. In some embodiments, the first set of patient position-shift vectors may be calculated by moving the acquired image relative to the treatment planning image to align or register the first patient target region of the treatment planning image with the first patient target region of the acquired image. For example, each voxel of the acquired image may be translated along or about the X, Y, and/or Z axes, maintaining the relative positions of each voxel of the acquired image to one another during movement of the acquired image, until the acquired image and the treatment planning image are approximately aligned with respect to the first patient target region (e.g., aligned within a predetermined acceptable tolerance or margin such that there is an acceptable area or proportion of overlap between the first patient target region in the images). The first set of patient position-shift vectors may then be calculated based on locational and/or positional differences between the acquired image before and after being moved into increased alignment with the treatment planning image. The first set of patient position-shift vectors may reflect the distance and/or direction each voxel of the acquired image is to be translated for acceptable alignment between the first patient target region of the acquired image and the first patient target region of the treatment planning image. Furthermore, the first set of patient position-shift vectors may include or correspond to instructions related to a first position and/or a first orientation of the patient (e.g., a first position and/or a first orientation of a surface on which the patient is disposed) so that the first patient target region of the patient is located in approximately the position that the first patient target region was in when the treatment planning images were acquired. This may facilitate the delivery of therapeutic radiation to the patient target region more closely to the treatment plan. Additionally, the first set of patient position-shift vectors may include information regarding any tilt, pitch, yaw, and/or roll corrections needed to be implemented via positioning of the patient platform and/or via adjusting the roll of a gantry to which the radiation source (e.g., a therapeutic radiation source) is coupled (e.g., for correcting a gantry firing position) such that the location of the first patient target region approximates the location of the first patient target region in the first treatment planning image.

In some embodiments, the acquired image of the first patient target region and the treatment planning image of the first patient target region may each be a two-dimensional image. The two-dimensional acquired image may be compared to the two-dimensional treatment planning image to calculate the first set of patient position-shift vectors. In some embodiments, a plurality of two-dimensional images of the first patient target region may be acquired along different orientations or planes (e.g., three or more orientations or planes), and the images may be compared to corresponding treatment planning images of the first patient target region that have been acquired along the same orientations or planes. Changes with respect to the position of the first patient target region along each image plane at each orientation may be used to calculate the first set of patient position-shift vectors. For example, the acquired images may include an acquired axial image, an acquired sagittal image, and an acquired coronal image of the first patient target region of the patient. When the patient is lying on a surface such as a patient platform or treatment couch in a supine position with the patient oriented such that the patient will encounter the therapeutic radiation source head first, the acquired axial image may be taken along an axial plane of the patient (e.g., the plane dividing the body into superior and inferior portions), the acquired sagittal image may be taken along a sagittal plane of the patient (e.g., the plane dividing the patient into right and left portions), and the acquired coronal image may be taken along a coronal plane of the patient (e.g., the plane dividing the patient into ventral and dorsal portions). The axial plane is disposed perpendicularly to the sagittal plane, and the coronal plane is disposed perpendicularly to both the axial plane and the sagittal plane. The treatment planning images may include a treatment planning axial image, a treatment planning sagittal image, and a treatment planning coronal image of the first patient target region of the patient. Thus, the acquired axial image corresponds to the treatment planning axial image, the acquired sagittal image corresponds to the treatment planning sagittal image, and the acquired coronal image corresponds to the treatment planning coronal image.

The amount the patient position and/or orientation should be adjusted along or about each of the X-, Y-, and Z-axes (e.g., via movement of the patient surface and/or rotating the radiation source) for treatment of the first patient target region may be reflected by the first set of patient position-shift vectors based on the differences between the treatment planning images and the respective acquired images taken within each of the axial, sagittal, and coronal planes of the patient. In some embodiments, the X-axis of the patient surface may be parallel to the intersection of the sagittal plane and the coronal plane of the patient and may be disposed in the sagittal plane. The Y-axis of the patient surface may be parallel to the intersection of the axial plane and the coronal plane of the patient and may be disposed in the axial plane. The Z-axis of the patient surface may be parallel to the intersection of the sagittal plane and the axial plane of the patient and may be disposed in the sagittal plane or the axial plane of the patient. To determine the first set of patient position-shift vectors, each of the acquired images of the first patient target region may be compared to a respective treatment planning image of the first patient target region taken within the same plane to determine a distance correction and/or rotation correction of the patient (e.g., via movement of the patient surface and/or rotation of the radiation source) within the same plane. One or more vectors of the first set of patient position-shift vectors may represent a magnitude and direction that the patient surface is to be moved (e.g., shifted and/or rotated) such that the first patient target region approximates the location of the first patient target region in the treatment planning images. One or more vectors of the first set of patient position-shift vectors may also represent a magnitude and direction that the radiation source may be moved (e.g., rotated on a gantry) such that the location of the first patient target region approximates the location of the first patient target region in the treatment planning images. In some embodiments, the first set of patient position-shift vectors may reflect up to six corrections (i.e., the amount of adjustment along or about each of the X-, Y-, and Z-axes of the patient platform). In some embodiments, DICOM Spatial Registration Objects (SROs) may be used to determine each of the six corrections (i.e., the amount of adjustment along or about each of the X-, Y-, and Z-axes of the patient platform) associated with the first set of patient position-shift vectors.

In some embodiments, the first set of patient position-shift vectors may be calculated by moving (e.g., via shifting and/or rotating) each acquired image relative to its respective treatment planning image to align or register the first patient target region of the treatment planning image with the first patient target region of the acquired image. Each acquired image may be shifted a particular distance and/or rotated a particular amount to improve the registration of the first patient target region of the treatment planning image with the first patient target region of the acquired image. For example, the image acquired along the axial plane at the time of treatment may be compared to a treatment planning image acquired along an axial plane of the patient to determine the amount of correction needed along the lateral axis (i.e., Y-axis) and vertical axis (i.e., Z-axis) of the patient surface (e.g., a platform or couch) within the axial plane and the amount of correction about the gantry roll axis (e.g., about the X-axis) needed. The image acquired along the sagittal plane at the time of treatment may be compared to a treatment planning image acquired along a sagittal plane of the patient to determine the amount of correction needed along the longitudinal axis (i.e., the X-axis) and the vertical axis and the amount of pitch correction (e.g., rotation about the Y-axis) of the patient surface (e.g., a platform or couch) within the sagittal plane. The image acquired along the coronal plane at the time of treatment may be compared to a treatment planning image acquired along a coronal plane of the patient to determine the amount of correction needed along the lateral axis and the longitudinal axis and the amount of yaw correction (i.e., about the Z-axis) of the patient surface (e.g., a platform or couch) within the coronal plane.

The first set of patient position-shift vectors may reflect the amount of correction of the patient surface needed along or about each of the X-, Y-, and Z-axes to improve the alignment between the first patient target region and the location of the first patient target region at the time of the acquisition of the treatment planning images. Thus, in some embodiments, the first set of patient position-shift vectors may include at least one patient position-shift vector reflecting an adjustment along the patient surface's X-axis based on the longitudinal differences determined from the comparison of the acquired sagittal image and the treatment planning sagittal image and/or the comparison of the acquired coronal image and the treatment planning coronal image. The first set of patient position-shift vectors may include at least one patient position-shift vector reflecting an adjustment along the patient surface's Y-axis based on the lateral differences determined from the comparison of the acquired axial image and the treatment planning axial image and/or the comparison of the acquired coronal image and the treatment planning coronal image. The first set of patient position-shift vectors may include at least one patient position-shift vector reflecting an adjustment along the patient surface's Z-axis based on the vertical differences determined from the comparison of the acquired axial image and the treatment planning axial image and/or the comparison of the acquired sagittal image and the treatment planning sagittal image. In some embodiments, the adjustment along the patient surface's Z-axis included in the first set of patient position-shift vectors may be an average of the lateral differences determined from the comparison of the acquired axial image and the treatment planning axial image and the lateral difference determined from the comparison of the acquired sagittal image and the treatment planning sagittal image.

With respect to rotation of the patient surface about the patient surface's axes and/or rotation of the radiation source about the radiation source's axes, the first set of patient position-shift vectors may include a rotational correction of the patient surface about the patient surface's Y-axis based on the comparison of the acquired sagittal image and the treatment planning sagittal image, and/or a rotational correction of the patient surface about the patient surface's Z-axis based on the comparison of the acquired coronal image and the treatment planning coronal image, and/or a rotational correction of the radiation source about the radiation source's X-axis (e.g., the gantry's X-axis which is coextensive with the patient surface's X-axis) based on the comparison of the acquired axial image and the treatment planning axial image. For example, shifting or panning an acquired sagittal or coronal image to match with the treatment planning sagittal or coronal image may translate to a set of patient position-shift vectors that represent shifts in the X-, Y-, and Z-axes. Tilting an acquired sagittal or coronal image to match with the treatment planning sagittal or coronal image may translate to a set of patient position-shift vectors that represent pitch and/or roll positional corrections. Thus, the amount the patient position or orientation should be adjusted along or about each of the X-, Y-, and Z-axes may be reflected by the first set of patient position-shift vectors based on the differences between the treatment planning images and the respective acquired images taken within each of the axial, sagittal, and coronal planes of the patient.

A second set of patient position-shift vectors may be calculated 106 based on the acquired image, a treatment planning image of the second patient target region (also referred to herein as a "second treatment planning image"), and the first set of patient position-shift vectors. In some embodiments, the second set of position-shift vectors may include distance and/or direction translations. In some embodiments, the direction translations may include tilt angles. In some embodiments, similarly as described above with respect to the first set of patient position-shift vectors, the second set of patient position-shift vectors may be calculated by moving the acquired image relative to the treatment planning image to align or register the second patient target region of the treatment planning image with the second patient target region of the acquired image. For example, each voxel of the acquired image may be translated along or about the X, Y, and/or Z axes, maintaining the relative positions of each voxel of the acquired image to one another during movement of the acquired image, until the acquired image and the treatment planning image have improved alignment with respect to the second patient target region (e.g., overlap between the second patient target region in the images is increased or optimized). The second set of patient position-shift vectors may then be calculated based on locational and/or positional differences between the acquired image before and after being moved into increased alignment with the treatment planning image. The second set of patient position-shift vectors may reflect the distance and/or direction each voxel of the acquired image had to be translated to improve the alignment between the second patient target region of the acquired image and the second patient target region of the treatment planning image. In some embodiments, the second set of position-shift vectors may be calculated based on the first set of patient position-shift vectors such that the distance and/or direction information included in the second set of position-shift vectors is relative to the first set of patient position-shift vectors, rather than to the initial coordinates of the voxels of the acquired image. Thus, the position and/or orientation instructions based on the second set of patient position-shift vectors may include or correspond to instructions reciting modifications to be made to the patient's position and/or orientation relative to the first position and/or the first orientation of the patient based on the first set of patient position-shift vectors such that the patient will be in a second position and/or orientation for irradiation of the second patient target region. Additionally, the second set of patient position-shift vectors may include information regarding any tilt, pitch, yaw, and roll corrections needed to be implemented via movement of the patient platform and/or via adjustment of the roll of a gantry to which the radiation source is coupled (e.g., correcting a gantry firing position) such that the second patient target region has improved alignment with the location of the second patient target region in the second treatment planning image.

In some embodiments, similarly as described above with respect to the first set of patient position-shift vectors, a plurality of two-dimensional images of the second patient target region may be acquired along different orientations or planes (e.g., three or more orientations or planes), and the images may be compared to corresponding treatment planning images of the second patient target that have been acquired along the same orientations or planes. In some embodiments, the plurality of two-dimensional images of the second patient target region may be the same two-dimensional images acquired of the first patient target region for calculating the first set of patient position-shift vectors. Changes with respect to the position of the second patient target region along each image plane at each orientation may be used to calculate the second set of patient position-shift vectors. For example, the acquired images may include an acquired axial image, an acquired sagittal image, and an acquired coronal image of the second patient target region of the patient. When the patient is lying on a surface such as a patient platform or treatment couch in a supine position with the patient oriented such that the patient will encounter the therapeutic radiation source head first, the acquired axial image may be taken along an axial plane of the patient (e.g., the plane dividing the body into superior and inferior portions), the acquired sagittal image may be taken along a sagittal plane of the patient (e.g., the plane dividing the patient into right and left portions), and the acquired coronal image may be taken along a coronal plane of the patient (e.g., the plane dividing the patient into ventral and dorsal portions). The axial plane is disposed perpendicularly to the sagittal plane, and the coronal plane is disposed perpendicularly to both the axial plane and the sagittal plane. The treatment planning images may include a treatment planning axial image, a treatment planning sagittal image, and a treatment planning coronal image of the second patient target region of the patient. Thus, the acquired axial image corresponds to the treatment planning axial image, the acquired sagittal image corresponds to the treatment planning sagittal image, and the acquired coronal image corresponds to the treatment planning coronal image.

The amount the patient position and/or orientation should be adjusted along or about each of the X-, Y-, and Z-axes (e.g., via movement of the patient surface and/or rotating the radiation source) for treatment of the second patient target region may be reflected by the second set of patient position-shift vectors based on the differences between the treatment planning images of the second patient target region and the respective acquired images of the second patient target region taken within each of the axial, sagittal, and coronal planes of the patient. In some embodiments, the X-axis of the patient surface may be parallel to the intersection of the sagittal plane and the coronal plane of the patient and may be disposed in the sagittal plane. The Y-axis of the patient surface may be parallel to the intersection of the axial plane and the coronal plane of the patient and may be disposed in the axial plane. The Z-axis of the patient surface may be parallel to the intersection of the sagittal plane and the axial plane of the patient and may be disposed in the sagittal plane or the axial plane of the patient. To determine the second set of patient position-shift vectors, each of the acquired images of the second patient target region may be compared to a respective treatment planning image of the second patient target region taken within the same plane to determine a distance correction and/or rotation correction of the patient (e.g., via movement of the patient surface and/or rotation of the radiation source) within the same plane. One or more vectors of the second set of patient position-shift vectors may represent a magnitude and direction that the patient surface is to be moved (e.g., shifted and/or rotated) such that the second patient target region approximates the location of the second patient target region in the treatment planning images. One or more vectors of the second set of patient position-shift vectors may also represent a magnitude and direction that the radiation source may be moved (e.g., rotated on a gantry) such that the location of the second patient target region approximates the location of the second patient target region in the treatment planning images. In some embodiments, the second set of patient position-shift vectors may reflect up to six corrections (i.e., the amount of adjustment along or about each of the X-, Y-, and Z-axes of the patient platform). In some embodiments, DICOM Spatial Registration Objects (SROs) may be used to determine each of the six corrections (i.e., the amount of adjustment along or about each of the X-, Y-, and Z-axes of the patient platform) associated with the second set of patient position-shift vectors.

In some embodiments, the second set of patient position-shift vectors may be calculated by moving (e.g., via shifting and/or rotating) each acquired image relative to its respective treatment planning image to align or register the second patient target region of the treatment planning image with the second patient target region of the acquired image. Each acquired image may be shifted a particular distance and/or rotated a particular amount to improve the registration of the second patient target region of the treatment planning image with the second patient target region of the acquired image. For example, the image acquired along an axial plane at the time of treatment may be compared to a treatment planning image acquired along an axial plane of the patient to determine the amount of correction needed along the lateral axis (i.e., Y-axis) and vertical axis (i.e., Z-axis) of the patient surface (e.g., a platform or couch) within the axial plane and the amount of correction about the gantry roll axis (e.g., about the X-axis) needed. The image acquired along a sagittal plane at the time of treatment may be compared to a treatment planning image acquired along a sagittal plane of the patient to determine the amount of correction needed along the longitudinal axis (i.e., the X-axis) and the vertical axis and the amount of pitch correction (e.g., rotation about the Y-axis) of the patient surface (e.g., a platform or couch) within the sagittal plane. The image acquired along a coronal plane at the time of treatment may be compared to a treatment planning image acquired along a coronal plane of the patient to determine the amount of correction needed along the lateral axis and the longitudinal axis and the amount of yaw correction (i.e., about the Z-axis) of the patient surface (e.g., a platform or couch) within the coronal plane.

The second set of patient position-shift vectors may reflect the amount of correction of the patient surface needed along or about each of the X-, Y-, and Z-axes to improve the alignment between the second patient target region and the location of the second patient target region at the time of the acquisition of the treatment planning images. Thus, in some embodiments, the second set of patient position-shift vectors may include at least one patient position-shift vector reflecting an adjustment along the patient surface's X-axis based on the longitudinal differences determined from the comparison of the acquired sagittal image and the treatment planning sagittal image and/or the comparison of the acquired coronal image and the treatment planning coronal image. The second set of patient position-shift vectors may include at least one patient position-shift vector reflecting an adjustment along the patient surface's Y-axis based on the lateral differences determined from the comparison of the acquired axial image and the treatment planning axial image and/or the comparison of the acquired coronal image and the treatment planning coronal image. The second set of patient position-shift vectors may include at least one patient position-shift vector reflecting an adjustment along the patient surface's Z-axis based on the vertical differences determined from the comparison of the acquired axial image and the treatment planning axial image and/or the comparison of the acquired sagittal image and the treatment planning sagittal image.

With respect to rotation of the patient surface about the patient surface's axes and/or rotation of the radiation source about the radiation source's axes, the second set of patient position-shift vectors may include a rotational correction of the patient surface about the patient surface's Y-axis based on the comparison of the acquired sagittal image and the treatment planning sagittal image, a rotational correction of the patient surface about the patient surface's Z-axis based on the comparison of the acquired coronal image and the treatment planning coronal image, and/or a rotational correction of the radiation source about the radiation source's X-axis (e.g., the gantry's X-axis which is coextensive with the patient surface's X-axis) based on the comparison of the acquired axial image and the treatment planning axial image. For example, shifting or panning an acquired sagittal or coronal image to match with the treatment planning sagittal or coronal image may translate to a set of patient position-shift vectors that represent shifts in the X-, Y-, and Z-axes. Tilting an acquired sagittal or coronal image to match with the treatment planning sagittal or coronal image may translate to a set of patient position-shift vectors that represent pitch and/or roll positional corrections. Thus, the amount the patient position or orientation should be adjusted along or about each of the X-, Y-, and Z-axes may be reflected by the second set of patient position-shift vectors based on the differences between the treatment planning images and the respective acquired images taken within each of the axial, sagittal, and coronal planes of the patient.

In some embodiments, the second set of patient position-shift vectors may reflect an amount of correction of the patient surface needed along or about each of the X-, Y-, and Z-axes relative to the position and/or orientation of the patient surface after being moved according to the first set of patient position-shift vectors to improve the alignment between the second patient target region and the location of the second patient target region at the time of the acquisition of the treatment planning images. Thus, in some embodiments, the amount the patient position or orientation should be adjusted along or about each of the X-, Y-, and Z-axes may be calculated by first determining the differences between the treatment planning images of the second patient target region and the respective acquired images of the second patient target region taken within each of the axial, sagittal, and coronal axes of the patient, and then accounting for the first set of patient position-shift vectors (e.g., subtracting the first set of patient position-shift vectors from the determined differences between the treatment planning images and the acquired images) such that the second set of position-shift vectors are relative to the first set of patient position-shift vectors. Thus, the surface on which the patient is disposed may transition from the position and/or orientation corresponding to the first set of patient position-shift vectors to the position and/or orientation corresponding to the second set of patient position-shift vectors without having to first be returned to the position and/or orientation of the surface at the time the treatment planning images were initially acquired.

In some embodiments, rather than comparing coordinate locations of a particular voxel of an acquired image to a treatment planning image or comparing three two-dimensional acquired images to three respective two-dimensional treatment planning images, the first set of patient position-shift vectors may be calculated by comparing a three-dimensional image acquired of the first patient target region to a three-dimensional treatment planning image of the first patient target region. The second set of patient position-shift vectors may be calculated by comparing the three-dimensional image acquired of the second patient target region (with may be the same image or a different image as the three-dimensional image acquired of the first patient target region) to a three-dimensional treatment planning image of the second patient target region and accounting for the first set of patient position-shift vectors (e.g., subtracting the first set of patient position-shift vectors from an intermediate set of patient position-shift vectors calculated via the comparison of the acquired image of the second patient target region to the treatment planning image of the second patient target region).

In some embodiments, the first and second sets of patient position-shift vectors may be calculated before a therapeutic radiation source is activated. In some embodiments, the first treatment planning image and the second treatment planning image are the same treatment planning image. In some embodiments, the first treatment planning image and the second treatment planning image are different treatment planning images.

In some embodiments, a first location difference and/or a second location difference may be calculated and used to determine if the corresponding tumors or tumor portions of the patient have changed shape, size, or location to the extent that the patient may not be able to be positioned or oriented to effectively or accurately receive radiation using the existing treatment plan. For example, the first location difference may be calculated by comparing a coordinate location of a particular voxel in the first patient target region in the acquired image with a coordinate location of a corresponding voxel of the first patient target region in the treatment planning image. The distance between the location of the particular voxel of the first patient target region in the acquired image and the location of the corresponding voxel of the first patient target region in the treatment planning image may be the first location difference. Similarly, the second location difference may be calculated by comparing a coordinate location of a particular voxel of the second patient target region in the acquired image with a coordinate location of a corresponding voxel in the second target region in the treatment planning image. The distance between the location of the particular voxel of the second patient target region in the acquired image with the location of the corresponding voxel of the second patient target region in the treatment planning image may be the second location difference. In some embodiments, the first location difference may be calculated by comparing a coordinate location within a two-dimensional image of a cross-section of a patient in the first patient target region in the acquired image with a coordinate location within a two-dimensional image of a cross-section of a patient in the first patient target region in the treatment planning image. The second location difference may be calculated by comparing a coordinate location within a two-dimensional image of a cross-section of a patient in the second patient target region in the acquired image with a coordinate location within a two-dimensional image of a cross-section of a patient in the second patient target region in the treatment planning image. The first location difference and the second location difference may be based on the direction and/or distance information included in the first set of patient position-shift vectors and the second set of patient position-shift vectors, respectively, described above. In some embodiments, the second location difference may be calculated based on the direction and/or distance information included in both the first set of patient position-shift vectors and the second set of patient position-shift vectors. In some embodiments, a notification may be generated and/or the radiation treatment session may be automatically paused if the first location difference and/or the second location difference exceed a location difference threshold. For example, the maximum corrective movement of the patient platform for lateral, longitudinal, and vertical corrections is about 3 cm, and the maximum corrective movement for rotation, pitch, and roll corrections are not to exceed 3°. In some embodiments, the maximum corrective movement of the patient platform for lateral, longitudinal, and vertical corrections and the maximum corrective movement for rotation, pitch, and roll corrections may be selected by a clinician or clinic. For example, the maximum corrective movement of the patient platform for lateral, longitudinal, and vertical corrections may be from about 1.5 cm to about 10 cm, and/or the maximum corrective movement for rotation, pitch, and roll corrections may be from about 2° to about 20°. Thus, the location difference threshold would be any location difference that would result in the corrective movement exceeding the maximum corrective movement of the patient platform in any respect.

The patient may be positioned according to the first set of patient position-shift vectors at a first location, at 108. In some embodiments, the patient may be positioned by moving a radiation therapy patient platform upon which the patient is disposed relative to a therapeutic radiation source according to the first set of patient position-shift vectors. For example, the platform may be tilted in any direction prior to irradiation, which may include translation of the platform in the tilted orientation relative to the therapeutic radiation source. In some embodiments, a radiation therapy patient platform upon which the patient is disposed may be moved along or about the radiation therapy patient platform's X-axis, Y-axis, and/or Z-axis (e.g., about a yaw, pitch, and/or roll axis). Furthermore, in some embodiments, the yaw and/or pitch of the radiation therapy patient platform may be adjusted. In some embodiments, a radiation therapy patient platform upon which the patient is disposed may be moved along the radiation therapy patient platform's X-axis, Y-axis, and/or Z-axis and about a yaw and/or pitch axis, while the radiation source may move about a roll axis (via movement of, for example, a gantry). As another example, transitioning the patient from the first location to the second location may include moving and/or bending a portion of the patient on the platform, such as a head, a knee or an elbow. The therapeutic radiation source may then be activated such that the first patient target region is irradiated.

In some embodiments, a roll correction to a patient position (e.g., as defined by the first set of patient position-shift vectors) may be implemented by rotating the radiation source (e.g., via rotating a gantry) in an opposite direction of the calculated roll correction. For example, if the roll correction to the patient position is 3° clockwise, the location of the radiation source may be adjusted to provide radiation from a gantry position (e.g., a gantry firing position) of −3° counter-clockwise relative to each requested radiation source delivery location. Therefore, if the treatment plan includes delivering radiation from the radiation source with a gantry at 0° based on the treatment planning images and the roll correction is 3° based on the differences between the treatment planning images and the acquired images, the radiation source may be adjusted 3° in the counterclockwise direction and deliver radiation (e.g., fire) from 357° rather than 0°.

The patient may then be positioned according to the second set of patient position-shift vectors such that the patient is transitioned from the first location to a second location, at 110. For example, the therapeutic radiation source may be deactivated such that the first patient target region is not irradiated by the therapeutic radiation source and then the patient may be positioned according to the second set of patient position-shift vectors. Similarly as described above, positioning the patient according to the second set of patient position-shift vectors may include moving a radiation therapy patient platform upon which the patient is disposed relative to a therapeutic radiation source and/or adjusting the rotational position of the radiation source according to the second set of patient position-shift vectors. The therapeutic radiation source may then be activated such that the second patient target region is irradiated. In some embodiments, for beam station-based delivery, the patient may be positioned according to the first set of patient position-shift vectors at the first location associated with a first beam station during a period of irradiation and the patient may be positioned according to the second set of patient position-shift vectors during a transition of the patient platform between the first location associated with the first beam station and the second location associated with a second beam station (e.g., a second beam station that is adjacent to the first beam station).

In some embodiments, rather than only defining a first patient target region and a second patient target region, the method may include defining any suitable number of target regions, acquiring images of each of the target regions, and positioning the patient based on position-shift vectors as described above based on the first patient target region and the second patient target region. For example, for beam station-based delivery, the method may include defining a plurality of patient target regions, where each patient target region may span across a plurality of beam stations. In some variations, there may be as many patient target regions as there are beam stations. Images may be acquired of each of the patient target regions, and a set of position-shift vectors associated with each defined patient target region may be generated as described above. Each patient target region and associated set of position-shift vectors can be associated with a particular beam station. During the transition of the patient and/or the patient platform to a location associated with each respective beam station, the patient may be positioned based on the set of position-shift vectors associated with that beam station. In some embodiments, the defined target regions (and associated sets of patient position-shift vectors) may be associated with more than one beam station such that a patient may be positioned based on a set of position-shift vectors and not repositioned as the patient platform advances through a series of two or more beam stations. Thus, the number of defined target regions (and associated respective sets of patient position-shift vectors) may be equal or less than the number of beam stations.

Figure 1B:
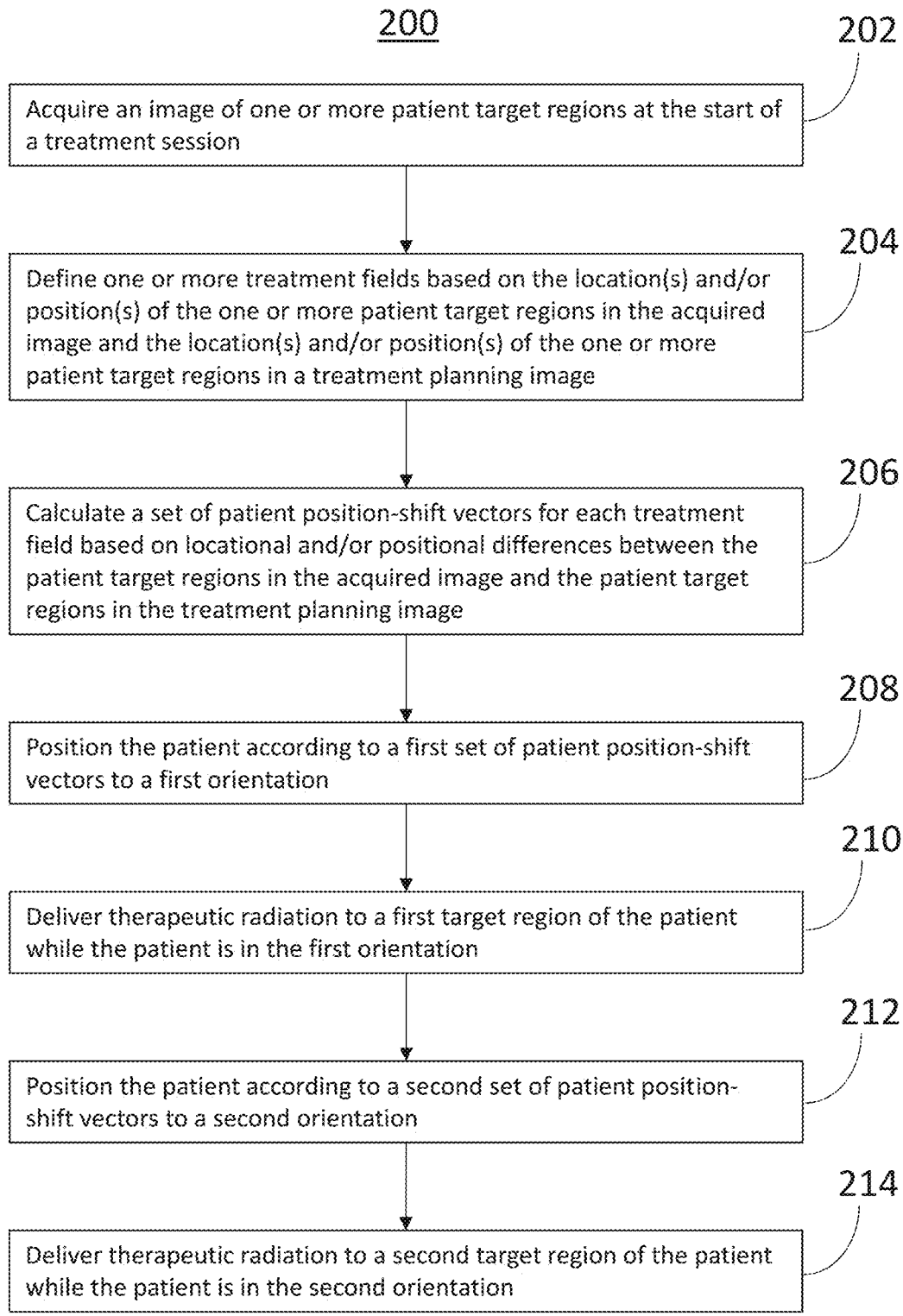
FIG. 1B is a flow chart illustrating a method, according to an embodiment.

FIG. 1B is a flow chart representation of one variation of a method 200 for patient setup. The method 200 comprises acquiring 202 an image of one or more patient target regions at the start of a radiation treatment session. In some embodiments, for example, a CT system may be used to acquire one or more images prior to or at the start of a treatment session. In some embodiments, the CT system may be attached to the same gantry as a radiation source intended for the delivery of radiation therapy during the treatment session. In some embodiments, the CT system may be attached to a separate gantry from the gantry supporting the radiation source. One or more treatment fields may be defined 204 based on the location(s) and/or position(s) of the one or more patient target regions in the acquired image and the location(s) and/or positions(s) of the one or more patient target regions in a treatment planning image. For example, the acquired image and/or the treatment planning image may be divided into a first treatment field and a second treatment field. Each treatment field may include one or more patient target regions such that the one or more patient target regions in the acquired image may be compared to one or more corresponding patient target regions in the treatment planning image. Each treatment field may correspond to a portion of a patient within which the one or more patient target regions are located that will be irradiated when a patient is positioned according to a particular setup during a particular portion of a radiation treatment session. A treatment field may map to series of patient platform positions or steps (e.g., beam stations) and/or a range of patient platform motion along its longitudinal axis where the one or more target regions in that treatment field intersect the radiation beam of the therapeutic radiation source. A treatment field may correspond with a particular patient position and/or platform orientation. For example, a first treatment field may be associated with a first patient position and orientation for irradiation of a first patient target region within the first treatment field and a second treatment field may be associated with a second patient position and orientation for irradiation of a second patient target region within the second treatment field. Thus, in some embodiments, the first treatment field may be associated with a first portion of a radiation treatment session (e.g., at a first beam station, and/or continuous or stepped movement of the patient platform through a first set of beam stations), a first patient target region, and a first position of the patient and the second treatment field may be associated with a second portion of the radiation treatment session (e.g., at a second beam station, and/or continuous or stepped movement of the patient platform through a second set of beam stations), a second patient target region, and a second position of the patient.

A set of patient position-shift vectors may be calculated 206 for each treatment field based on locational and/or positional differences between the patient target regions in the acquired image and the patient target regions in the treatment planning image. The location of the patient target regions in the acquired image may be compared with a location of the patient target regions in the treatment planning image in 2D and/or 3D. In embodiments in which two treatment fields have been defined, a first set of patient position-shift vectors may be calculated for the first treatment field and a second set of patient position-shift vectors may be calculated for the second treatment field. Each set of position-shift vectors may include distance and/or direction translations. In some embodiments, the direction translations may include tilt angles. In some embodiments, the first set of patient position-shift vectors may be calculated by moving the acquired image relative to the treatment planning image to align or register the first patient target region of the treatment planning image with the first patient target region of the acquired image. For example, in some embodiments, the first patient target region may be divided into sub-regions (e.g., sub-volumes) that may be represented by voxels, and the coordinates of each voxel of the first patient target region of the acquired image may be compared with the coordinates of a corresponding voxel of the first patient target region in the treatment planning image. For example, each voxel of the acquired image may be translated along or about the X, Y, and/or Z axes, maintaining the relative positions of each coordinate of each voxel of the acquired image to one another during movement of the acquired image, until the acquired image and the treatment planning image have improved alignment with respect to the first patient target region (e.g., overlap between the first patient target region in the images is increased or optimized). The first set of patient position-shift vectors may then be calculated based on locational and/or positional differences between the acquired image before and after being moved into increased alignment with the treatment planning image. The first set of patient position-shift vectors may reflect the distance and/or direction each voxel of the acquired image had to be translated to improve the alignment between the first patient target region of the acquired image and the first patient target region of the treatment planning image. Furthermore, the first set of patient position-shift vectors may include or correspond to instructions related to a first position and/or a first orientation of the patient (e.g., a first position and/or a first orientation of a surface on which the patient is disposed) so that the first patient target region of the patient is located in approximately the position that the first patient target region was in when the treatment planning images were acquired. This may facilitate the delivery of therapeutic radiation to the patient target region more closely to the treatment plan. Additionally, the first set of patient position-shift vectors may include information regarding any tilt, pitch, yaw, and/or roll corrections needed to be implemented via positioning of the patient platform such that the location of the first patient target region approximates the location of the first patient target region in the first treatment planning image.

In some embodiments, the acquired image of the first patient target region and the treatment planning image of the first patient target region may each be a two-dimensional image. The two-dimensional acquired image may be compared to the two-dimensional treatment planning image to calculate the first set of patient position-shift vectors. In some embodiments, a plurality of two-dimensional images of the first patient target region may be acquired along different orientations or planes (e.g., three or more orientations or planes), and the images may be compared to corresponding treatment planning images of the first patient target region that have been acquired along the same orientations or planes. Changes with respect to the position of the first patient target region along each image plane at each orientation may be used to calculate the first set of patient position-shift vectors. For example, the acquired images may include an acquired axial image, an acquired sagittal image, and an acquired coronal image of the first patient target region of the patient. When the patient is lying on a surface such as a patient platform or treatment couch in a supine position with the patient oriented such that the patient will encounter the therapeutic radiation source head first, the acquired axial image may be taken along an axial plane of the patient (e.g., the plane dividing the body into superior and inferior portions), the acquired sagittal image may be taken along a sagittal plane of the patient (e.g., the plane dividing the patient into right and left portions), and the acquired coronal image may be taken along a coronal plane of the patient (e.g., the plane dividing the patient into ventral and dorsal portions). The axial plane is disposed perpendicularly to the sagittal plane, and the coronal plane is disposed perpendicularly to both the axial plane and the sagittal plane. The treatment planning images may include a treatment planning axial image, a treatment planning sagittal image, and a treatment planning coronal image of the first patient target region of the patient. Thus, the acquired axial image corresponds to the treatment planning axial image, the acquired sagittal image corresponds to the treatment planning sagittal image, and the acquired coronal image corresponds to the treatment planning coronal image.

The amount the patient position and/or orientation should be adjusted along or about each of the X-, Y-, and Z-axes (e.g., via movement of the patient surface and/or rotating the radiation source) for treatment of the first patient target region may be reflected by the first set of patient position-shift vectors based on the differences between the treatment planning images and the respective acquired images taken within each of the axial, sagittal, and coronal planes of the patient. In some embodiments, the X-axis of the patient surface may be parallel to the intersection of the sagittal plane and the coronal plane of the patient and may be disposed in the sagittal plane. The Y-axis of the patient surface may be parallel to the intersection of the axial plane and the coronal plane of the patient and may be disposed in the axial plane. The Z-axis of the patient surface may be parallel to the intersection of the sagittal plane and the axial plane of the patient and may be disposed in the sagittal plane or the axial plane of the patient. To determine the first set of patient position-shift vectors, each of the acquired images of the first patient target region may be compared to a respective treatment planning image of the first patient target region taken within the same plane to determine a distance correction and/or rotation correction of the patient (e.g., via movement of the patient surface and/or rotation of the radiation source) within the same plane. One or more vectors of the first set of patient position-shift vectors may represent a magnitude and direction that the patient surface is to be moved (e.g., shifted and/or rotated) such that the first patient target region approximates the location of the first patient target region in the treatment planning images. One or more vectors of the first set of patient position-shift vectors may also represent a magnitude and direction that the radiation source may be moved (e.g., rotated on a gantry) such that the location of the first patient target region approximates the location of the first patient target region in the treatment planning images. In some embodiments, the first set of patient position-shift vectors may reflect up to six corrections (i.e., the amount of adjustment along or about each of the X-, Y-, and Z-axes of the patient platform). In some embodiments, DICOM Spatial Registration Objects (SROs) may be used to determine each of the six corrections (i.e., the amount of adjustment along or about each of the X-, Y-, and Z-axes of the patient platform) associated with the first set of patient position-shift vectors.

In some embodiments, the first set of patient position-shift vectors may be calculated by moving (e.g., via shifting and/or rotating) each acquired image relative to its respective treatment planning image to align or register the first patient target region of the treatment planning image with the first patient target region of the acquired image. Each acquired image may be shifted a particular distance and/or rotated a particular amount to improve the registration of the first patient target region of the treatment planning image with the first patient target region of the acquired image. For example, the image acquired along an axial plane at the time of treatment may be compared to a treatment planning image acquired along an axial plane of the patient to determine the amount of correction needed along the lateral axis (i.e., Y-axis) and vertical axis (i.e., Z-axis) of the patient surface (e.g., a platform or couch) within the axial plane and the amount of correction about the gantry roll axis (e.g., about the X-axis) needed. The image acquired along a sagittal plane at the time of treatment may be compared to a treatment planning image acquired along a sagittal plane of the patient to determine the amount of correction needed along the longitudinal axis (i.e., the X-axis) and the vertical axis and the amount of pitch correction (e.g., rotation about the Y-axis) of the patient surface (e.g., a platform or couch) within the sagittal plane. The image acquired along a coronal plane at the time of treatment may be compared to a treatment planning image acquired along a coronal plane of the patient to determine the amount of correction needed along the lateral axis and the longitudinal axis and the amount of yaw correction (i.e., about the Z-axis) of the patient surface (e.g., a platform or couch) within the coronal plane.

The first set of patient position-shift vectors may reflect the amount of correction of the patient surface needed along or about each of the X-, Y-, and Z-axes to improve the alignment between the first patient target region and the location of the first patient target region at the time of the acquisition of the treatment planning images. Thus, in some embodiments, the first set of patient position-shift vectors may include at least one patient position-shift vector reflecting an adjustment along the patient surface's X-axis based on the longitudinal differences determined from the comparison of the acquired sagittal image and the treatment planning sagittal image and/or the comparison of the acquired coronal image and the treatment planning coronal image. The first set of patient position-shift vectors may include at least one patient position-shift vector reflecting an adjustment along the patient surface's Y-axis based on the lateral differences determined from the comparison of the acquired axial image and the treatment planning axial image and/or the comparison of the acquired coronal image and the treatment planning coronal image. The first set of patient position-shift vectors may include at least one patient position-shift vector reflecting an adjustment along the patient surface's Z-axis based on the vertical differences determined from the comparison of the acquired axial image and the treatment planning axial image and/or the comparison of the acquired sagittal image and the treatment planning sagittal image.

With respect to rotation of the patient surface about the patient surface's axes and/or rotation of the radiation source about the radiation source's axes, the first set of patient position-shift vectors may include a rotational correction of the patient surface about the patient surface's Y-axis based on the comparison of the acquired sagittal image and the treatment planning sagittal image, a rotational correction of the patient surface about the patient surface's Z-axis based on the comparison of the acquired coronal image and the treatment planning coronal image, and/or a rotational correction of the radiation source about the radiation source's X-axis (e.g., the gantry's X-axis which is coextensive with the patient surface's X-axis) based on the comparison of the acquired axial image and the treatment planning axial image. For example, shifting or panning an acquired sagittal or coronal image to match with the treatment planning sagittal or coronal image may translate to a set of patient position-shift vectors that represent shifts in the X-, Y-, and Z-axes. Tilting an acquired sagittal or coronal image to match with the treatment planning sagittal or coronal image may translate to a set of patient position-shift vectors that represent pitch and/or roll positional corrections. Thus, the amount the patient position or orientation should be adjusted along or about each of the X-, Y-, and Z-axes may be reflected by the first set of patient position-shift vectors based on the differences between the treatment planning images and the respective acquired images taken within each of the axial, sagittal, and coronal planes of the patient.

In some embodiments, similarly as described above with respect to the first set of patient position-shift vectors, the second set of patient position-shift vectors may be calculated by moving the acquired image relative to the treatment planning image to align the second patient target region of the treatment planning image with the second patient target region of the acquired image. For example, in some embodiments, the second patient target region may be divided into sub-regions (e.g., sub-volumes) that may be represented by voxels, and the coordinates of each voxel of the second patient target region of the acquired image may be compared with the coordinates of a corresponding voxel of the second patient target region in the treatment planning image. For example, each voxel of the acquired image may be translated along or about the X, Y, and/or Z axes, maintaining the relative positions of each voxel of the acquired image to one another during movement of the acquired image, until the acquired image and the treatment planning image have improved alignment with respect to the second patient target region (e.g., overlap between the second patient target region in the images is increased or optimized). The second set of patient position-shift vectors may then be calculated based on locational and/or positional differences between the acquired image before and after being moved into increased alignment with the treatment planning image. The second set of patient position-shift vectors may reflect the distance and/or direction each voxel of the acquired image had to be translated to improve the alignment between the second patient target region of the acquired image and the second patient target region of the treatment planning image. In some embodiments, the second set of position-shift vectors may be calculated based on the first set of patient position-shift vectors such that the distance and/or direction information included in the second set of position-shift vectors is relative to the first set of patient position-shift vectors, rather than to the initial coordinates of the voxels of the acquired image. Thus, the position and/or orientation instructions based on the second set of patient position-shift vectors may include or correspond to instructions reciting modifications to be made to the patient's position and/or orientation relative to the first position and/or the first orientation of the patient based on the first set of patient position-shift vectors such that the patient will be in a second position and/or orientation for irradiation of the second patient target region. Additionally, the second set of patient position-shift vectors may include information regarding any tilt, pitch, yaw, and roll corrections needed to be implemented via movement of the patient platform and/or via adjustment of the roll of a gantry to which the radiation source is coupled (e.g., correcting a gantry firing position) such that the second patient target region has improved alignment with the location of the first patient target region in the first treatment planning image.

In some embodiments, similarly as described above with respect to the first set of patient position-shift vectors, a plurality of two-dimensional images of the second patient target region may be acquired along different orientations or planes (e.g., three or more orientations or planes), and the images may be compared to corresponding treatment planning images of the second patient target that have been acquired along the same orientations or planes. In some embodiments, the plurality of two-dimensional images of the second patient target region may be the same two-dimensional images acquired of the first patient target region for calculating the first set of patient position-shift vectors. Changes with respect to the position of the second patient target region along each image plane at each orientation may be used to calculate the second set of patient position-shift vectors. For example, the acquired images may include an acquired axial image, an acquired sagittal image, and an acquired coronal image of the second patient target region of the patient. When the patient is lying on a surface such as a patient platform or treatment couch in a supine position with the patient oriented such that the patient will encounter the therapeutic radiation source head first, the acquired axial image may be taken along an axial plane of the patient (e.g., the plane dividing the body into superior and inferior portions), the acquired sagittal image may be taken along a sagittal plane of the patient (e.g., the plane dividing the patient into right and left portions), and the acquired coronal image may be taken along a coronal plane of the patient (e.g., the plane dividing the patient into ventral and dorsal portions). The axial plane is disposed perpendicularly to the sagittal plane, and the coronal plane is disposed perpendicularly to both the axial plane and the sagittal plane. The treatment planning images may include a treatment planning axial image, a treatment planning sagittal image, and a treatment planning coronal image of the second patient target region of the patient. Thus, the acquired axial image corresponds to the treatment planning axial image, the acquired sagittal image corresponds to the treatment planning sagittal image, and the acquired coronal image corresponds to the treatment planning coronal image.

The amount the patient position and/or orientation should be adjusted along or about each of the X-, Y-, and Z-axes (e.g., via movement of the patient surface and/or rotating the radiation source) for treatment of the second patient target region may be reflected by the second set of patient position-shift vectors based on the differences between the treatment planning images of the second patient target region and the respective acquired images of the second patient target region taken within each of the axial, sagittal, and coronal planes of the patient. In some embodiments, the X-axis of the patient surface may be parallel to the intersection of the sagittal plane and the coronal plane of the patient and may be disposed in the sagittal plane. The Y-axis of the patient surface may be parallel to the intersection of the axial plane and the coronal plane of the patient and may be disposed in the axial plane. The Z-axis of the patient surface may be parallel to the intersection of the sagittal plane and the axial plane of the patient and may be disposed in the sagittal plane or the axial plane of the patient. To determine the second set of patient position-shift vectors, each of the acquired images of the second patient target region may be compared to a respective treatment planning image of the second patient target region taken within the same plane to determine a distance correction and/or rotation correction of the patient (e.g., via movement of the patient surface and/or rotation of the radiation source) within the same plane. One or more vectors of the second set of patient position-shift vectors may represent a magnitude and direction that the patient surface is to be moved (e.g., shifted and/or rotated) such that the second patient target region approximates the location of the second patient target region in the treatment planning images. One or more vectors of the second set of patient position-shift vectors may also represent a magnitude and direction that the radiation source may be moved (e.g., rotated on a gantry) such that the location of the second patient target region approximates the location of the second patient target region in the treatment planning images. In some embodiments, the second set of patient position-shift vectors may reflect up to six corrections (i.e., the amount of adjustment along or about each of the X-, Y-, and Z-axes of the patient platform). In some embodiments, DICOM Spatial Registration Objects (SROs) may be used to determine each of the six corrections (i.e., the amount of adjustment along or about each of the X-, Y-, and Z-axes of the patient platform) associated with the second set of patient position-shift vectors.

In some embodiments, the second set of patient position-shift vectors may be calculated by moving (e.g., via shifting and/or rotating) each acquired image relative to its respective treatment planning image to align or register the second patient target region of the treatment planning image with the second patient target region of the acquired image. Each acquired image may be shifted a particular distance and/or rotated a particular amount to improve the registration of the second patient target region of the treatment planning image with the second patient target region of the acquired image. For example, the image acquired along an axial plane at the time of treatment may be compared to a treatment planning image acquired along an axial plane of the patient to determine the amount of correction needed along the lateral axis (i.e., Y-axis) and vertical axis (i.e., Z-axis) of the patient surface (e.g., a platform or couch) within the axial plane and the amount of correction about the gantry roll axis (e.g., about the X-axis) needed. The image acquired along a sagittal plane at the time of treatment may be compared to a treatment planning image acquired along a sagittal plane of the patient to determine the amount of correction needed along the longitudinal axis (i.e., the X-axis) and the vertical axis and the amount of pitch correction (e.g., rotation about the Y-axis) of the patient surface (e.g., a platform or couch) within the sagittal plane. The image acquired along a coronal plane at the time of treatment may be compared to a treatment planning image acquired along a coronal plane of the patient to determine the amount of correction needed along the lateral axis and the longitudinal axis and the amount of yaw correction (i.e., about the Z-axis) of the patient surface (e.g., a platform or couch) within the coronal plane.

The second set of patient position-shift vectors may reflect the amount of correction of the patient surface needed along or about each of the X-, Y-, and Z-axes to improve the alignment between the second patient target region and the location of the second patient target region at the time of the acquisition of the treatment planning images. Thus, in some embodiments, the second set of patient position-shift vectors may include at least one patient position-shift vector reflecting an adjustment along the patient surface's X-axis based on the longitudinal differences determined from the comparison of the acquired sagittal image and the treatment planning sagittal image and/or the comparison of the acquired coronal image and the treatment planning coronal image. The second set of patient position-shift vectors may include at least one patient position-shift vector reflecting an adjustment along the patient surface's Y-axis based on the lateral differences determined from the comparison of the acquired axial image and the treatment planning axial image and/or the comparison of the acquired coronal image and the treatment planning coronal image. The second set of patient position-shift vectors may include at least one patient position-shift vector reflecting an adjustment along the patient surface's Z-axis based on the vertical differences determined from the comparison of the acquired axial image and the treatment planning axial image and/or the comparison of the acquired sagittal image and the treatment planning sagittal image.

With respect to rotation of the patient surface about the patient surface's axes and/or rotation of the radiation source about the radiation source's axes, the second set of patient position-shift vectors may include a rotational correction of the patient surface about the patient surface's Y-axis based on the comparison of the acquired sagittal image and the treatment planning sagittal image, a rotational correction of the patient surface about the patient surface's Z-axis based on the comparison of the acquired coronal image and the treatment planning coronal image, and/or a rotational correction of the radiation source about the radiation source's X-axis (e.g., the gantry's X-axis which is coextensive with the patient surface's X-axis) based on the comparison of the acquired axial image and the treatment planning axial image. For example, shifting or panning an acquired sagittal or coronal image to match with the treatment planning sagittal or coronal image may translate to a set of patient position-shift vectors that represent shifts in the X-, Y-, and Z-axes. Tilting an acquired sagittal or coronal image to match with the treatment planning sagittal or coronal image may translate to a set of patient position-shift vectors that represent pitch and/or roll positional corrections. Thus, the amount the patient position or orientation should be adjusted along or about each of the X-, Y-, and Z-axes may be reflected by the second set of patient position-shift vectors based on the differences between the treatment planning images and the respective acquired images taken within each of the axial, sagittal, and coronal planes of the patient.

In some embodiments, the second set of patient position-shift vectors may reflect an amount of correction of the patient surface needed along or about each of the X-, Y-, and Z-axes relative to the position and/or orientation of the patient surface after being moved according to the first set of patient position-shift vectors to improve the alignment between the second patient target region and the location of the second patient target region at the time of the acquisition of the treatment planning images. Thus, in some embodiments, the amount the patient position or orientation should be adjusted along or about each of the X-, Y-, and Z-axes may be calculated by first determining the differences between the treatment planning images of the second patient target region and the respective acquired images of the second patient target region taken within each of the axial, sagittal, and coronal axes of the patient, and then accounting for the first set of patient position-shift vectors (e.g., subtracting the first set of patient position-shift vectors from the determined differences between the treatment planning images and the acquired images) such that the second set of position-shift vectors are relative to the first set of patient position-shift vectors. Thus, the surface on which the patient is disposed may transition from the position and/or orientation corresponding to the first set of patient position-shift vectors to the position and/or orientation corresponding to the second set of patient position-shift vectors without having to first be returned to the position and/or orientation of the surface at the time the treatment planning images were initially acquired.

In some embodiments, rather than comparing coordinate locations of a particular voxel of an acquired image to a treatment planning image or comparing three two-dimensional acquired images to three respective two-dimensional treatment planning images, the first set of patient position-shift vectors may be calculated by comparing a three-dimensional image acquired of the first patient target region to a three-dimensional treatment planning image of the first patient target region. The second set of patient position-shift vectors may be calculated by comparing the three-dimensional image acquired of the second patient target region (with may be the same image or a different image as the three-dimensional image acquired of the first patient target region) to a three-dimensional treatment planning image of the second patient target region and accounting for the first set of patient position-shift vectors (e.g., subtracting the first set of patient position-shift vectors from an intermediate set of patient position-shift vectors calculated via the comparison of the acquired image of the second patient target region to the treatment planning image of the second patient target region).

The patient may be positioned 208 according to a first set of patient position-shift vectors to a first orientation. The positioning may include, for example, arranging the patient in a particular pose on a patient platform and/or orienting or tilting the patient platform in any suitable direction according to the first set of patient position-shift vectors. Therapeutic radiation may be delivered 210 to a first target region of the patient while the patient is in the first orientation, as further described below.

The patient may be positioned 212 according to the second set of patient position-shift vectors to a second orientation. The positioning may include, for example, arranging the patient in a particular pose on a patient platform and/or orienting or tilting the patient platform in any suitable direction according to the second set of patient position-shift vectors. Therapeutic radiation may then be delivered 214 to the second target region of the patient while the patient is in the second orientation.

In some embodiments, the patient may be moved continuously relative to a source of therapeutic radiation while therapeutic radiation is delivered to the patient. For example, the patient may be positioned in the first orientation via rotating and/or tilting the patient platform and/or rotating a gantry on which the source of therapeutic radiation is disposed. The patient platform may then be continuously moved relative to (e.g., through) a radiation beam path or beam plane of a therapeutic radiation source such that radiation is delivered to the first target region of the patient. After delivery of the radiation to the first target region of the patient, the patient may be positioned in the second orientation via rotating and/or tilting the patient platform and/or rotating the gantry on which the source of therapeutic radiation is disposed. The patient platform may then be continuously moved relative to (e.g., through) the radiation beam path or beam plane of the therapeutic radiation source such that radiation is delivered to the second target region of the patient.

In some embodiments, the patient may be moved through a series of discrete, predefined positions relative to the therapeutic radiation source and the radiation may be delivered when the patient is stationary relative to the therapeutic radiation source. For example, the patient may be moved to the first orientation and positioned relative to the therapeutic radiation source such that the patient is immobilized and stationary relative to the therapeutic radiation source. Radiation beams may then be applied to the first patient target region of the patient for a particular length of time and/or during a first series of stepped movements of the patient platform relative to the therapeutic radiation source. In variations where the therapeutic radiation source is mounted on a rotatable gantry that rotates around the patient, radiation may be applied over one or more rotations or cycles around the patient. For example, in a circular, continuously rotating gantry, radiation may be applied over several rotations of the therapeutic radiation source around the patient. After a patient target region has been irradiated according to the treatment plan, the beam of radiation may be turned off and the patient platform may be moved to the next predefined position, and radiation may be applied to the patient as described above (and repeated as desired). Thus, after radiation beams have been applied to the first target region according to the treatment plan, the platform and/or the patient may be adjusted so that the patient is transitioned to the second orientation and position. When in the second orientation and position, the patient may be immobilized and stationary relative to the therapeutic radiation source. Radiation beams may then be applied to the second target region of the patient for a particular length of time, during a second series of stepped movements of the patient platform relative to the therapeutic radiation source, and/or for application of radiation to the second target region over on or more rotations or cycles of a rotatable gantry (similarly as described above). After the second patient target region has been irradiated according to the treatment plan, the beam of radiation may be turned off. If there are additional patient target regions to be irradiated, the patient and/or the patient platform may be adjusted to the next predefined position. Additional details and variations of a radiation therapy system comprising methods of radiation delivery is described in U.S. Provisional Appl. No. 62/562,212, filed Sep. 22, 2017, which is herein incorporated by reference in its entirety.

In some embodiments, the user may specify criterion limiting the automatic application of setup correction to avoid clinically inaccurate position corrections and/or unfeasible position corrections. For example, the user may set a threshold time duration from the time of image acquisition to irradiation. The threshold time duration may be based on the time period during which the acquired image is still likely to be accurate. If the time threshold elapses, the user may be alerted and the radiation treatment session halted. Similarly, the user may limit automatic application of setup correction based on elapsed treatment time. Thus, if the calculated position of the target or targets are only likely to be consistent for a certain time duration, the user may set a limit on the treatment time duration before the radiation treatment session must be discontinued and/or fresh/updated images of the target region or target regions acquired. Another criterion that may be included is the distance between target regions or targeted tumors may be limited such that if the distance between the target regions or target tumors exceeds a distance threshold, the user may be notified prior to the initiation of the radiation treatment session. The distance may be based on the distance at which accuracy of the position of one or both of the target regions is likely inaccurate. In some embodiments, the distance threshold may be based on clinical protocol. For example, the distance threshold may be about 30 cm. Additionally, the amount of monitor units (MU) delivered may be used to determine if the system is likely to provide clinically inaccurate position corrections. For example, a notification may be provided to the user prior to the initiation of the radiation treatment session based on the total MU planned to be delivered.

Furthermore, in some embodiments, if a set of patient shift vectors is generated and the corresponding patient position is not feasible, a notification to the user may be generated and/or adjustments may be made. For example, if the set of patient shift vectors suggests a tilt angle that is too steep of an incline to be able to be safely implemented, the user may be notified and/or adjustments made. Additionally, if the set of patient shift vectors suggests a positioning of the patient and/or platform that would result in a collision with another portion of the patient therapy system, the user may be notified and/or adjustments made. In some embodiments, the system may be configured to notify the user and/or make adjustments based on predetermined thresholds and/or boundary conditions, such as pre-determine platform incline thresholds or boundaries representing the locations of other system components. In some embodiments, alternative positioning instructions may be generated representing, for example, alternative tilt angles. In some embodiments, notifications representing the effect of the alternative positioning instructions may be generated (e.g., representing that a particular number of degrees different in the tilt angle changes alignment with a patient target region by a particular amount) for the user's consideration.

Figure 2A:
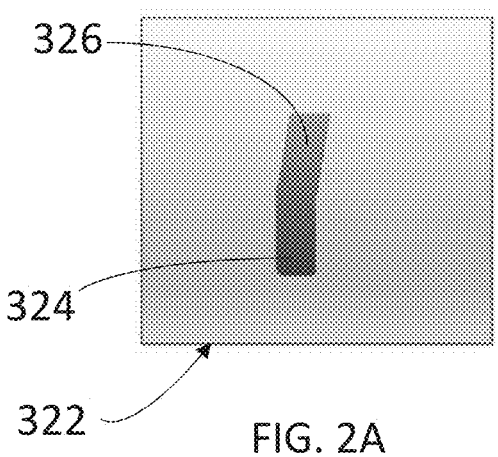
FIGS. 2A-2F illustrate a procedure by which the position of a patient may be adjusted, according to an embodiment.
Figure 2B:
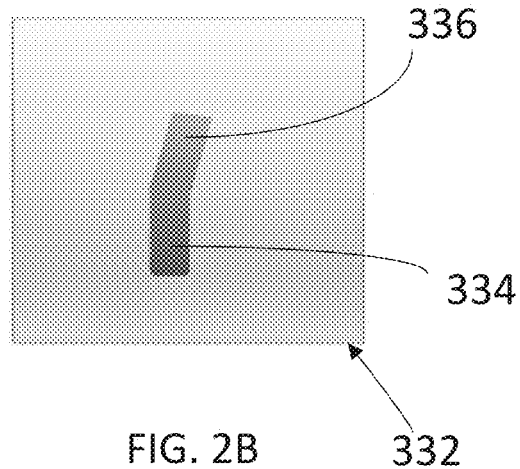

FIGS. 2A-2F illustrate a procedure by which the position of a patient may be adjusted. For example, FIG. 2A represents a treatment planning image 322 acquired in advance of a radiation treatment session. The treatment planning image 322 may be used to prepare a treatment plan for irradiating a tumor of the patient during a radiation treatment session. As shown, the treatment planning image 322 may include a first patient target region 324 and a second patient target region 326, representing a first portion and a second portion of a tumor, respectively. FIG. 2B represents an acquired image 332 acquired via imaging prior to or at the start of a radiation treatment session. The acquired image 332 may include a first patient target region 334 and a second patient target region 336, representing the first portion and the second portion of the tumor, respectively. The treatment planning image 322 and the acquired image 332 may be acquired via any suitable imaging method, such as, for example, via PET or CT scans. The treatment planning image 322 and the acquired image 332 may be two-dimensional images.

Figure 2C:
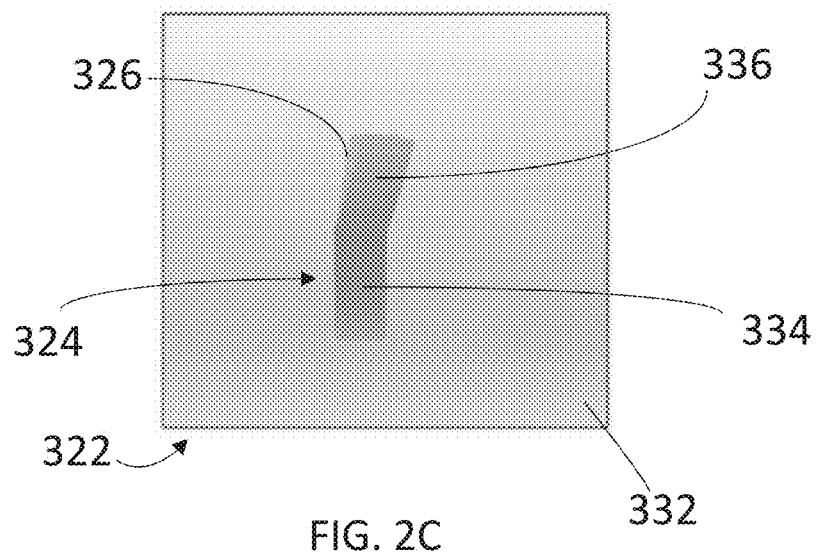

FIG. 2C is a representation of the acquired image 332 overlapped with the treatment planning image 322 such that the shape, size, and location of the first patient target region 324 and the second patient target region 326 of the treatment planning image 322 may be compared to the shape, size, and location of the first patient target region 334 and the second patient target region 336 of the acquired image 332. As shown in FIG. 2C, the first patient target region 324 and the second patient target region 326 of the treatment planning image 322 and the first patient target region 334 and the second patient target region 336 of the acquired image 332 are not aligned or perfectly coincident. In particular, the first patient target region 324 of the treatment planning image 322 and the first patient target region 334 of the acquired image 332 are co-located and appear to align, but the second patient target region 326 of the treatment planning image 322 and the second patient target region 336 of the acquired image 332 are not co-located. As may be seen in FIG. 2C, the second patient target region 336 of the acquired image 332 is disposed at an angle relative to the second patient target region 326 of the treatment planning image 322. The accuracy of the treatment plan may be improved by positioning and orienting the patient such that the second patient target region of the patient is co-located or more closely co-located with the location of the second patient target region 326 of the treatment planning image 322 for the delivery of radiation to the second patient target region.

Figure 2D:
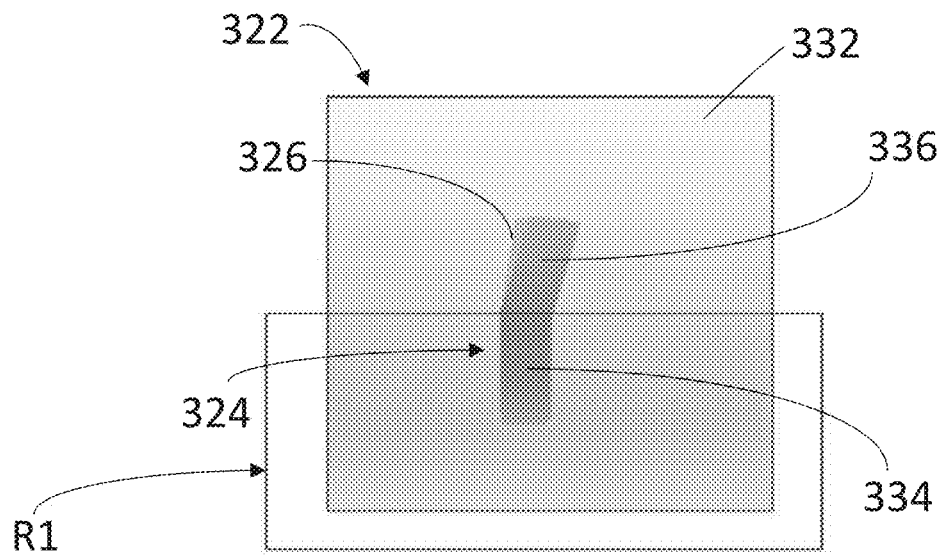

One or more treatment fields may be defined based on the location and position of each portion of the acquired image 332 and the location and position of each portion of the treatment planning image 322. As shown in FIG. 2D, the user may specify a first treatment field R1 (e.g., via a graphic user interface associated with a radiation therapy system). Since the first patient target region 324 of the treatment planning image 322 and the first patient target region 324 of the acquired image 332 are shown to be co-located and coextensive in the initial comparison shown in FIG. 2C, no locational and/or positional differences exist between the treatment planning image 322 and the acquired image 332 within the first treatment field R1. Thus, no position-shifting is necessary prior to delivery of therapeutic radiation to the patient within the first treatment field R1. In some embodiments, a first set of patient position-shift vectors may be calculated for the first treatment field R1 reflecting that no translation along or about the X, Y, and Z axes (e.g., about a yaw, pitch, and/or roll axis) is necessary during patient set up prior to initiation of the delivery of therapeutic radiation to the first patient target region. For example, in some embodiments, the first patient target region may be divided into sub-regions (e.g., sub-volumes) that may be represented by voxels, and the coordinates of each voxel of the first patient target region 334 of the acquired image 332 may be compared with the coordinates of a corresponding voxel of the first patient target region 324 in the treatment planning image 322. If the first set of patient position-shift vectors reflects new coordinate locations for each voxel of the acquired image 332 corresponding to the differences between the acquired image 332 and the treatment planning image 322 by including a position-change vector for each voxel of the acquired image 332, the position-shift vectors corresponding to the first treatment field R1 may be reflected as zeros. In some embodiments, rather than dividing the first patient target region into sub-regions for comparison of the locations of the sub-regions in the acquired image 332 to the treatment planning image 322, the first set of patient position-shift vectors may reflect distance and/or direction the acquired image 332 may be moved (e.g., translated and/or rotated) relative to the treatment planning image 322 in the same plane to improve the alignment (e.g., overlap) between the first patient target region 324 and the second patient target region 326. If no movement of the acquired image 332 relative to the treatment planning image 322 would improve the alignment between the first patient target region 324 and the second patient target region 326, the first set of position-change vectors corresponding to the first treatment field R1 may be reflected as zeros.

Figure 2E:
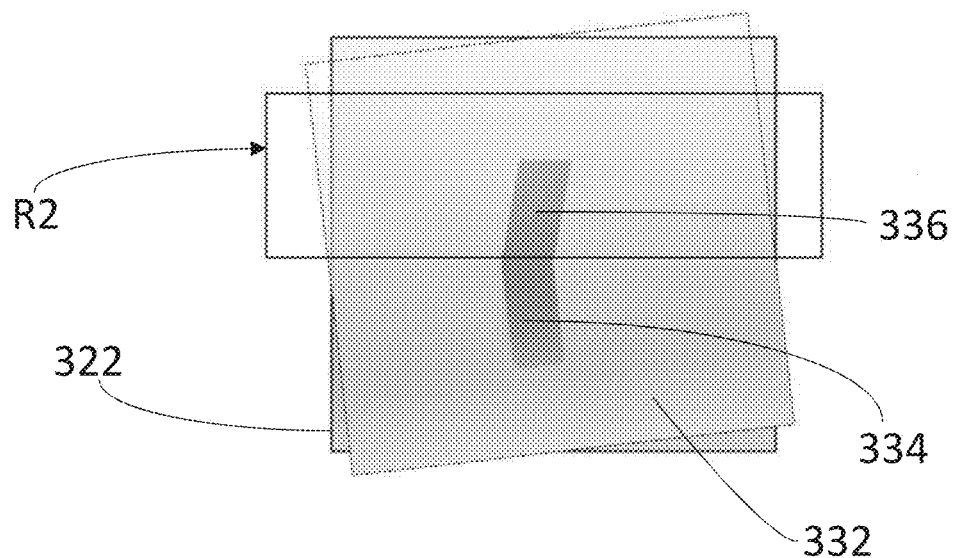

As shown in FIG. 2E, the user may specify a second treatment field R2. The acquired image 332 may be moved relative to the treatment planning image 322 to align the treatment planning image 322 with the acquired image 332 within in the second treatment field R2. In some embodiments, the second patient target region may be divided into sub-regions (e.g., sub-volumes) that may be represented by voxels, and the coordinates of each voxel of the second patient target region 336 of the acquired image 332 may be compared with the coordinates of a corresponding voxel of the second patient target region 326 in the treatment planning image 322. For example, each voxel of the acquired image 332 may be translated along or about the X, Y, and/or Z axes until the second patient target region 326 of the treatment planning image 322 and the second patient target region 336 of the acquired image 332 are aligned and/or co-located. For example, as shown in FIG. 2E, the acquired image 332 may be rotated counterclockwise relative to the treatment planning image 322 until the treatment planning image 322 and the acquired image 332 are aligned and/or the overlap between the second patient target region 336 and the second patient target region 326 is increased within the second treatment field R2. A second set of patient position-shift vectors may be calculated corresponding to the second treatment field R2 based on locational and/or positional differences between the treatment planning image 322 and the acquired image 332 in the second treatment field R2 prior to the movement of the acquired image 332 to improve the overlap with the treatment planning image 322. In some embodiments, the second set of patient position-shift vectors may reflect the distance and/or direction each voxel of the acquired image 332 is translated to improve the alignment between the second patient target region 336 and the second patient target region 326. In some embodiments, the second set of patient position-shift vectors may reflect the distance and/or direction the acquired image 332 may be translated and/or rotated relative to the treatment planning image 322 in the same plane to improve the alignment (e.g., overlap) between the second patient target region 336 and the second patient target region 326. Furthermore, the second set of patient position-shift vectors may include and/or correspond to instructions as to how a patient should be positioned and oriented for the delivery of therapeutic radiation (e.g., via the positioning and/or orienting of a platform upon which the patient is disposed) such that the second target region of the patient may be irradiated more accurately than if the patient is arranged in the position they were in during the acquisition of treatment planning images (e.g., if the platform on which the patient is disposed is in the same position and/or orientation as during the acquisition of the treatment planning images).

Figure 2F:
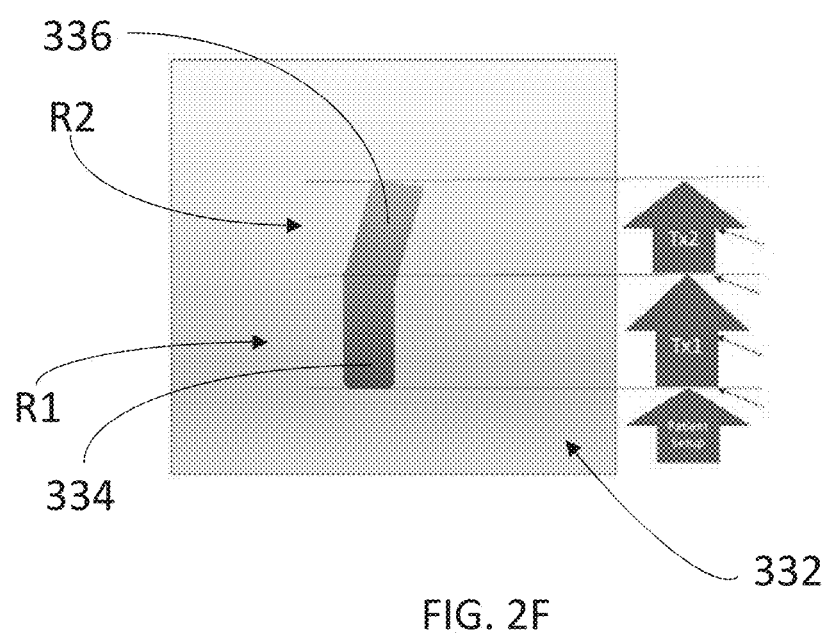

As represented in FIG. 2F, the patient may then be positioned relative to a therapeutic radiation source of a radiation therapy system such that radiation may be applied effectively to the target regions of the patient. For example, the patient may be positioned in a first orientation according to the first set of patient position-shift vectors during patient setup. In this case, the first set of patient position-shift vectors represent no locational or positional differences from the first patient target region 324 in the treatment planning image 322 to the first patient target region 334 in the acquired image 332. Thus, the patient may be positioned according to the treatment plan as represented in the treatment planning image 322. Next, therapeutic radiation may be delivered to the first patient target region while the patient is in the first orientation (e.g., while translating the patient through the radiation therapy system relative to the therapeutic radiation source or while the patient platform is stationary at a particular beam station), as represented by arrow Tx1.

After delivering therapeutic radiation to the first patient target region while the patient is in the first orientation, the delivery of therapeutic radiation may be ceased and the patient may be positioned in a second orientation according to the second set of patient position-shift vectors. Next, therapeutic radiation may be delivered to the second patient target region while the patient is in the second orientation (e.g., while translating the patient through the radiation therapy system relative to the therapeutic radiation source or while the patient platform is stationary at a particular beam station adjacent to the beam station associated with the patient's first orientation), as represented by arrow Tx2.

Figure 3A:
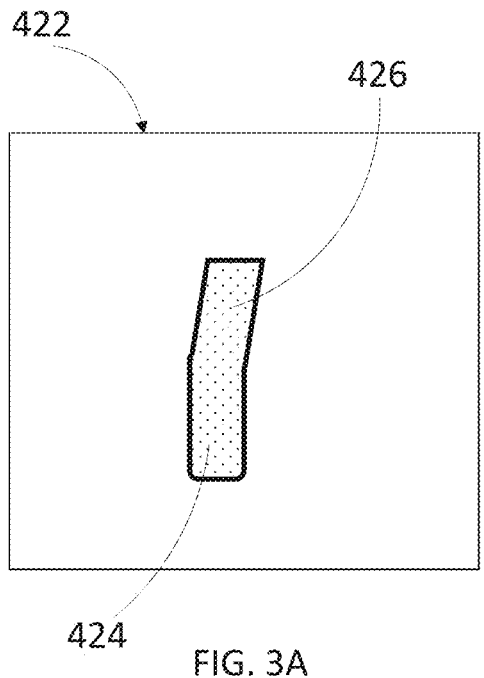
FIGS. 3A-3F illustrate a procedure by which the position of a patient may be adjusted, according to an embodiment.
Figure 3B:
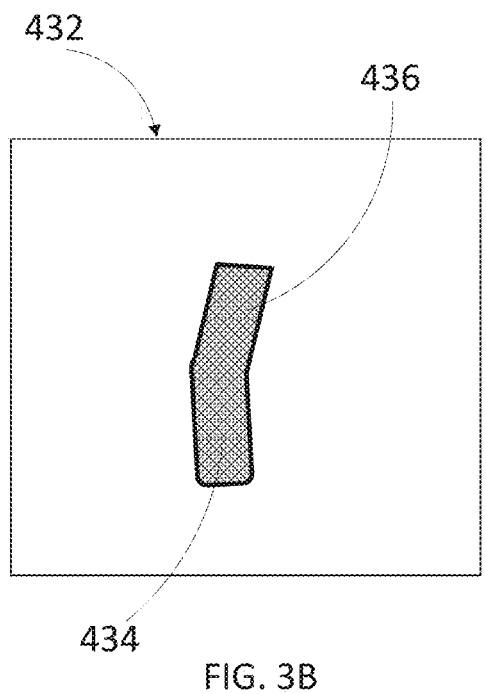

FIGS. 3A-3F illustrate a procedure by which the position of a patient may be adjusted. For example, FIG. 3A represents a treatment planning image 422 acquired in advance of a radiation treatment session. The treatment planning image 422 may be used to generate a treatment plan for irradiating a tumor of the patient during a radiation treatment session. As shown, the treatment planning image 422 may include a first patient target region 424 and a second patient target region 426, representing a first portion and a second portion of a tumor, respectively. FIG. 3B represents an acquired image 432 acquired via imaging prior to or at the start of a radiation treatment session. The acquired image 432 may include a first patient target region 434 and a second patient target region 436, representing the first portion and the second portion of the tumor, respectively. The treatment planning image 422 and the acquired image 432 may be acquired via any suitable imaging method, such as, for example, via PET or CT scans. The treatment planning image 422 and the acquired image 432 may be two-dimensional images.

Figure 3C:
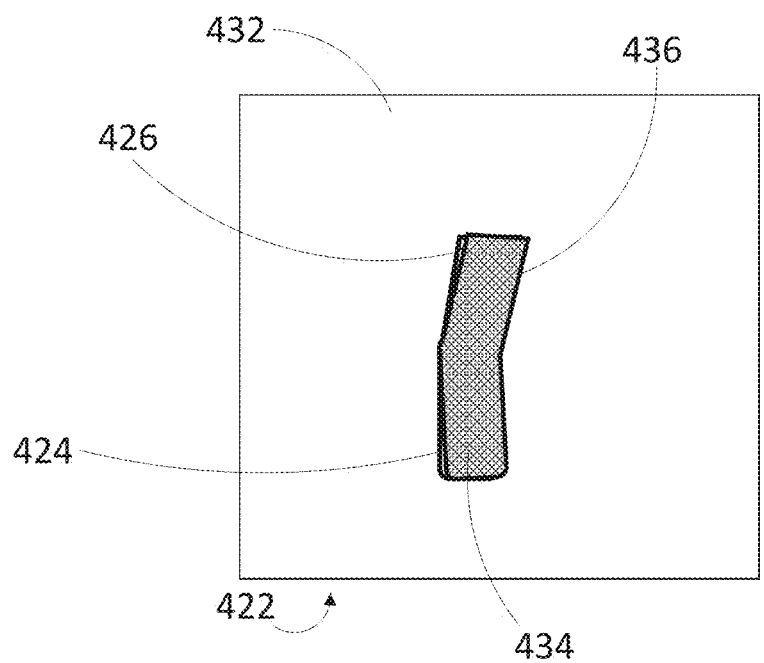

FIG. 3C is a representation of the acquired image 432 overlapped with the treatment planning image 422 such that the shape, size, and location of the first patient target region 424 and the second patient target region 426 of the treatment planning image 422 may be compared to the shape, size, and location of the first patient target region 434 and the second patient target region 424 of the acquired image 432. As shown in FIG. 3C, the first patient target region 424 and the second patient target region 426 of the treatment planning image 422 are not aligned or perfectly coincident with the first patient target region 434 and the second patient target region 436, respectively, of the acquired image 432. As may be seen in FIG. 3C, the first patient target region 434 and the second patient target region 436 of the acquired image 432 are each disposed at an angle relative to the first patient target region 424 and the second patient target region 426, respectively, of the treatment planning image 422. Thus, the accuracy of the treatment plan may be improved by positioning and/or orienting the patient such that the first patient target region is co-located or more closely co-located with the location of the first patient target region 424 of the treatment planning image 422 for the delivery of radiation to the first patient target region, and to reposition and/or reorient the patient such that the second patient target region of the patient is co-located or more closely co-located with the location of the second patient target region 426 of the treatment planning image 422 for the delivery of radiation to the second patient target region.

Figure 3D:
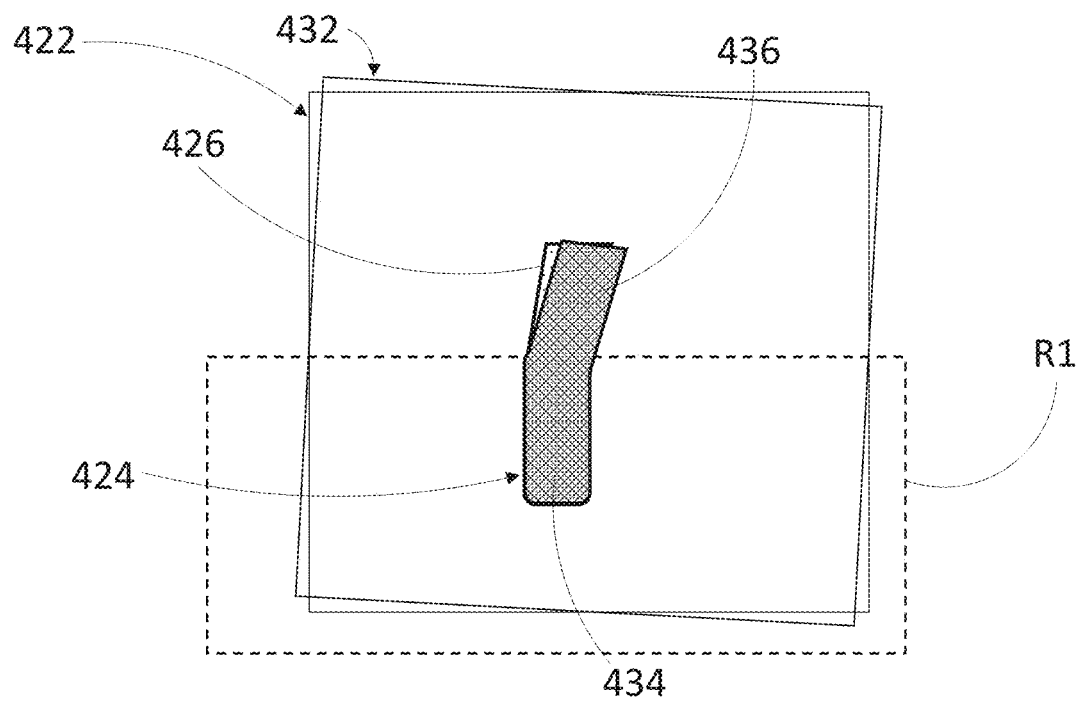

One or more treatment fields may be defined based on the location and position of each portion of the acquired image 432 and the location and position of each portion of the treatment planning image 422. As shown in FIG. 3D, the user may specify a first treatment field R1 (e.g., via a graphic user interface associated with a radiation therapy system). The acquired image 432 may be moved relative to the treatment planning image 422 to align the treatment planning image 422 with the acquired image 432 within in the first treatment field R1. In some embodiments, the first patient target region may be divided into sub-regions (e.g., sub-volumes) that may be represented by voxels, and the coordinates of each voxel of the first patient target region 434 of the acquired image 432 may be compared with the coordinates of a corresponding voxel of the first patient target region 424 in the treatment planning image 422. For example, each voxel of the acquired image 432 may be translated along or about the X, Y, and/or Z axes until the acquired image 432 and the treatment planning image 422 are aligned and/or co-located. For example, as shown in FIG. 3D, the acquired image 432 may be rotated clockwise relative to the treatment planning image 422 until the treatment planning image 422 and the acquired image 432 are aligned and/or the overlap between the first patient target region 424 and the first patient target region 426 is increased within the first treatment field R1. A first set of patient position-shift vectors may be calculated corresponding to the first treatment field R1 based on locational and/or positional differences between the treatment planning image 422 and the acquired image 432 in the first treatment field R1 prior to the movement of the acquired image 432 to improve the overlap with the treatment planning image 422. The first set of patient position-shift vectors may reflect the distance and/or direction each voxel of the acquired image 432 is translated to improve the alignment between the first patient target region 434 of the acquired image 432 and the first patient target region 424 of the treatment planning image 422. In some embodiments, rather than dividing the first patient target region into sub-regions for comparison of the locations of the sub-regions in the acquired image 432 to the treatment planning image 422, the first set of patient position-shift vectors may reflect the distance and/or direction the acquired image 432 may be moved (e.g., translated and/or rotated) relative to the treatment planning image 422 in the same plane to improve the alignment (e.g., overlap) between the first patient target region 424 and the first patient target region 426. Furthermore, the first set of patient position-shift vectors may include and/or correspond to instructions as to a first position and/or orientation of the patient for the delivery of therapeutic radiation (e.g., via the positioning and/or orienting of a platform upon which the patient is disposed) such that the first patient target region of the patient may be irradiated more accurately than if the patient is arranged in the position they were in during the acquisition of treatment planning images (e.g., if the platform on which the patient is disposed is in the same position and/or orientation as during the acquisition of the treatment planning images).

Figure 3E:
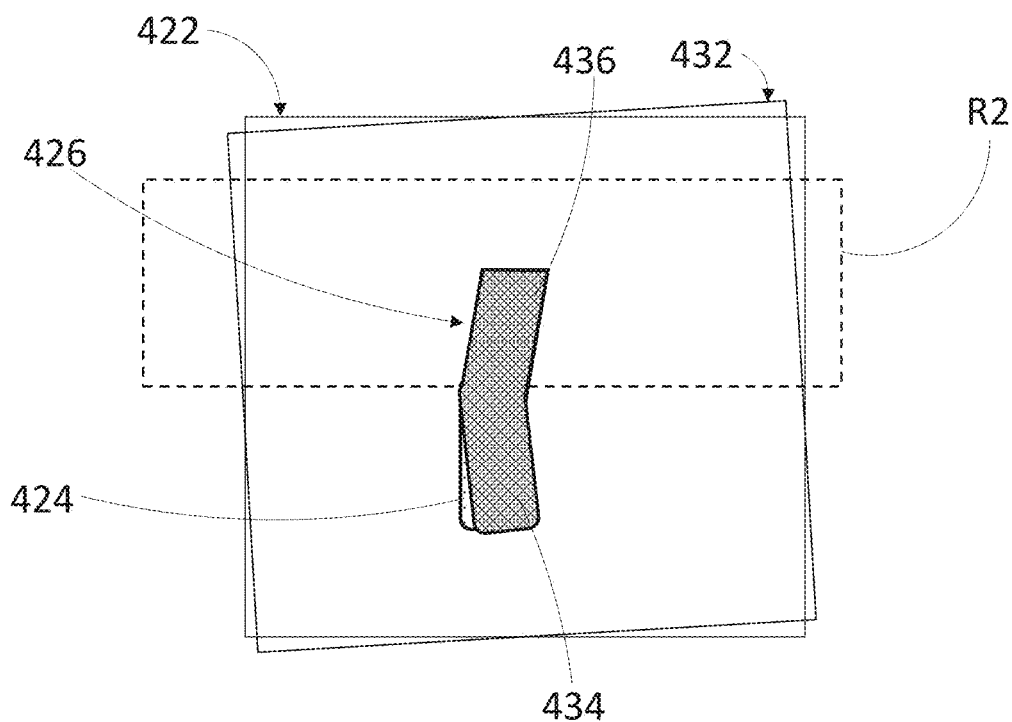

As shown in FIG. 3E, the user may specify a second treatment field R2. Similarly as described above with reference to FIG. 3D, the acquired image 432 may be moved relative to the treatment planning image 422 to align and/or co-located the treatment planning image 422 with the acquired image 432 within in the second treatment field R2. In some embodiments, the second patient target region may be divided into sub-regions (e.g., sub-volumes) that may be represented by voxels, and the coordinates of each voxel of the second patient target region 436 of the acquired image 432 may be compared with the coordinates of a corresponding voxel of the second patient target region 426 in the treatment planning image 422. As shown in FIG. 3E, the acquired image 432 may be rotated counterclockwise relative to the treatment planning image 422 until the treatment planning image 422 and the acquired image 432 are aligned and/or the overlap between the second patient target region 426 and the second patient target region 436 is increased within the second treatment field R2. A second set of patient position-shift vectors may be calculated corresponding to the second treatment field R2 based on locational and/or positional differences between the treatment planning image 422, the acquired image 432 in the second treatment field R2, and the first set of patient position-shift vectors. For example, the second set of patient position-shift vectors may be calculated based on the differences between the treatment planning image 422 and the acquired image 432 prior to the movement of the acquired image 432 to improve the overlap with the treatment planning image 422. In some embodiments, the second set of patient position-shift vectors may reflect the distance and/or direction each voxel of the acquired image 432 is translated to improve the alignment between the second patient target region 436 of the acquired image 432 and the second patient target region 426 of the treatment planning image 422. In some embodiments, the second set of patient position-shift vectors may reflect the distance and/or direction the acquired image 432 may be translated and/or rotated relative to the treatment planning image 422 in the same plane to improve the alignment (e.g., overlap) between the second patient target region 436 and the second patient target region 426. The second set of patient position-shift vectors may be calculated based on the first set of patient position-shift vectors in that, after determining a preliminary set of position shift vectors reflecting the differences between the treatment planning image 422 and the acquired image 432, the second set of patient position-shift vectors may be calculated based on the first position and/or orientation of the patient during irradiation of the first patient target region of the patient. Furthermore, the second set of patient position-shift vectors may include instructions for repositioning and/or reorienting the patient (e.g., via the positioning and/or orienting of a platform upon which the patient is disposed) for the delivery of therapeutic radiation based on the first position/orientation of the patient.

Figure 3F:
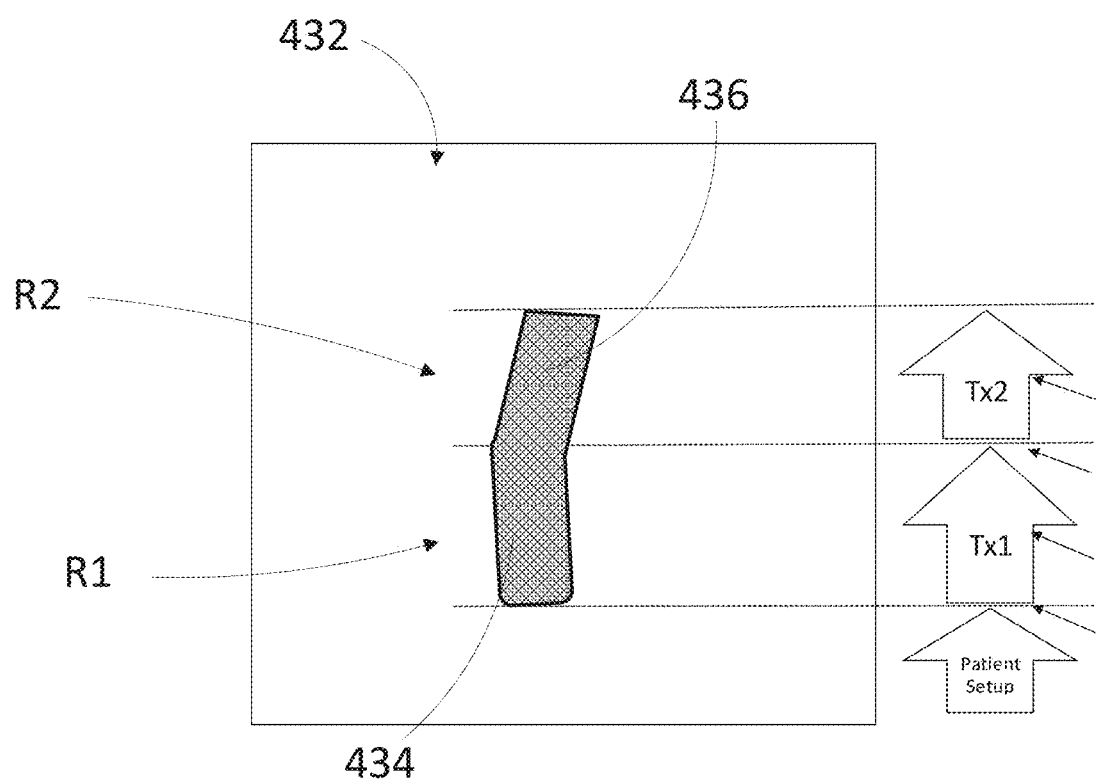

As represented in FIG. 3F, the patient may then be positioned relative to a therapeutic radiation source of a radiation therapy system such that radiation may be applied effectively to the target regions of the patient. For example, the patient may be positioned in a first orientation on the patient platform according to the first set of patient position-shift vectors during patient setup. Therapeutic radiation may then be delivered to the first patient target region while the patient is in the first orientation and moved through a range of patient platform positions into the radiation beam of the therapeutic radiation source, as represented by arrow Tx1. For example, a first range or set of patient platform movements (e.g., beam stations) may correspond to the irradiation of the first patient target region and a second range or set of patient platform movements (e.g., beam stations) may correspond to the irradiation of the second patient target region. Thus, the platform may move through the first range set of patient platform movements (e.g., a first set of patient platform steps or positions) relative to the therapeutic radiation source in the first orientation and with the patient arranged in the first position on the patient platform while the therapeutic radiation is delivered. The patient platform may move continuously during the delivery of therapeutic radiation, or may stop at a series of beam stations where therapeutic radiation is delivered when the platform is stationary at a beam station. In some embodiments, rather than the first orientation of the patient being associated with a first set of patient platform movements, the first orientation may be associated with only one patient platform step or position (e.g., a beam station).

After delivering therapeutic radiation to the first patient target region while the patient is in the first orientation, the delivery of therapeutic radiation may be ceased and the patient may be positioned in a second orientation according to the second set of patient position-shift vectors. For example, the patient platform may cease progressing through the system and the user may be notified to adjust the setup position. Next, therapeutic radiation may be delivered to the second patient target region while the patient is in the second orientation and moved through a range of patient platform positions into the radiation beam of the therapeutic radiation source, as represented by arrow Tx2. For example, the platform may move through a second range or set of patient platform movements (e.g., a second range or set of patient platform steps or positions, or beam stations) relative to the therapeutic radiation source in the second orientation and with the patient arranged in the second position orientation on the patient platform while the therapeutic radiation is delivered. In some embodiments, rather than the second orientation of the patient being associated with a second set of patient platform movements, the second orientation may be associated with only one patient platform step or position (e.g., beam station adjacent to a beam station associated with the first orientation).

Figure 4A:
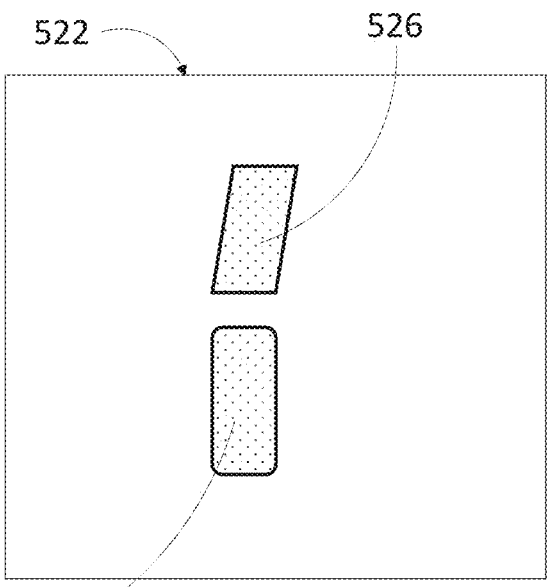
FIGS. 4A-4F illustrate a procedure by which the position of a patient may be adjusted to irradiate two discrete patient target regions, according to an embodiment.
Figure 4B:
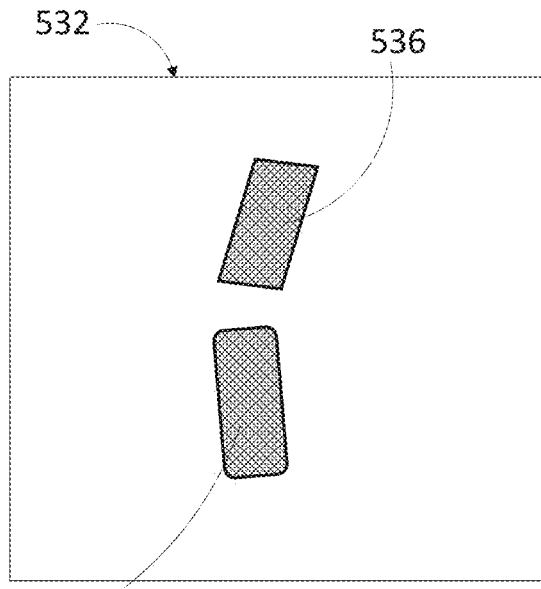

FIGS. 4A-4F illustrate a procedure by which the position of a patient may be adjusted. For example, FIG. 4A represents a treatment planning image 522 acquired in advance of a radiation treatment session. The treatment planning image 522 may be used to prepare a treatment plan for irradiating two or more tumors of the patient, e.g., tumors located at different body regions of a patient, during a radiation treatment session. For example, the tumors may be located in a patient's head and chest or in a patient's neck and lungs. As shown, the treatment planning image 522 may include a first patient target region 524 and a second patient target region 526, representing a first tumor and a second tumor, respectively. FIG. 4B represents an acquired image 532 acquired via imaging prior to or at the start of a radiation treatment session. The acquired image 532 may include a first patient target region 534 and a second patient target region 536, representing the first tumor and the second tumor, respectively. As may be seen in the representative treatment planning image 522 and the acquired image 532 of FIGS. 4A and 4B, respectively, the first tumor and the second tumor have different shapes, with the first tumor having rounded edges and the second tumor having sharp edges. The treatment planning image 522 and the acquired image 532 may be acquired via any suitable imaging method, such as, for example, via PET or CT scans. The treatment planning image 522 and the acquired image 532 may be two-dimensional images.

Figure 4C:
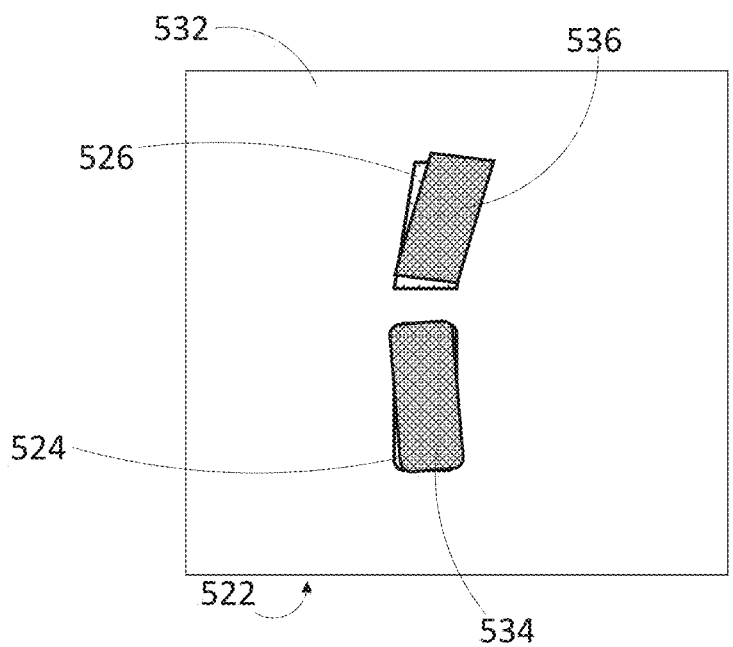

FIG. 4C is a representation of the acquired image 532 overlapped with the treatment planning image 522 such that the shape, size, and location of the first patient target region 524 and the second patient target region 526 of the treatment planning image 522 may be compared to the shape, size, and location of the first patient target region 534 and the second patient target region 536 of the acquired image 532. As shown in FIG. 4C, the first patient target region 524 and the second patient target region 526 of the treatment planning image 522 are not aligned or perfectly coincident with the first patient target region 534 and the second patient target region 536, respectively, of the acquired image 532. As may be seen in FIG. 4C, the first patient target region 534 and the second patient target region 536 of the acquired image 532 are each disposed at an angle relative to the first patient target region 524 and the second patient target region 526, respectively, of the treatment planning image 522. Thus, the accuracy of the treatment plan may be improved by positioning and/or orienting the patient such that the first patient target region is co-located or more closely co-located with the location of the first patient target region 524 of the treatment planning image 522 for the delivery of radiation to the first patient target region, and to reposition and/or reorient the patient such that the second patient target region of the patient is co-located or more closely co-located with the location of the second patient target region 526 of the treatment planning image 522 for the delivery of radiation to the second patient target region.

Figure 4D:
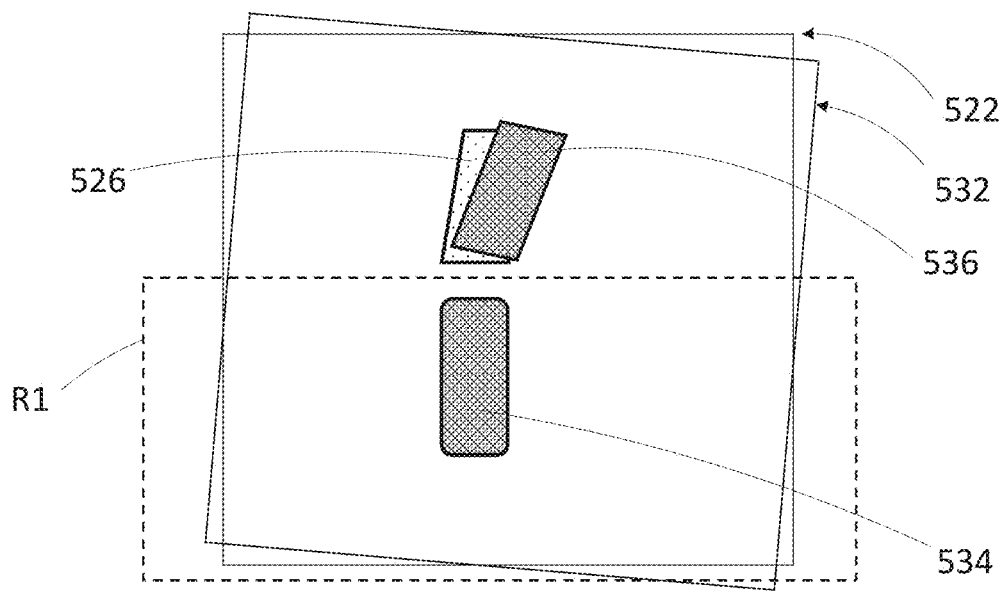

One or more treatment fields may be defined based on the location and position of each portion of the acquired image 532 and the location and position of each portion of the treatment planning image 522. As shown in FIG. 4D, the user may specify a first treatment field R1 (e.g., via a graphic user interface associated with a radiation therapy system). The acquired image 532 may be moved relative to the treatment planning image 522 to align the treatment planning image 522 with the acquired image 532 within in the first treatment field R1. In some embodiments, the first patient target region may be divided into sub-regions (e.g., sub-volumes) that may be represented by voxels, and the coordinates of each voxel of the first patient target region 534 of the acquired image 532 may be compared with the coordinates of a corresponding voxel of the first patient target region 524 in the treatment planning image 522. For example, each voxel of the acquired image 532 may be translated along or about the X, Y, and/or Z axes until the acquired image 532 and the treatment planning image 522 are aligned and/or co-located. For example, as shown in FIG. 4D, the acquired image 532 may be rotated clockwise relative to the treatment planning image 522 until the treatment planning image 522 and the acquired image 532 are aligned and/or the overlap between the first patient target region 524 and the first patient target region 534 is increased within the first treatment field R1. A first set of patient position-shift vectors may be calculated corresponding to the first treatment field R1 based on locational and/or positional differences between the treatment planning image 522 and the acquired image 532 in the first treatment field R1 prior to the movement of the acquired image 532 to improve the overlap with the treatment planning image 522. The first set of patient position-shift vectors may reflect the distance and/or direction each voxel of the acquired image 532 is translated to improve the alignment between the first patient target region 534 of the acquired image 532 and the first patient target region 524 of the treatment planning image 522. In some embodiments, rather than dividing the first patient target region into sub-regions for comparison of the locations of the sub-regions in the acquired image 532 to the treatment planning image 522, the first set of patient position-shift vectors may reflect the distance and/or direction the acquired image 532 may be moved (e.g., translated and/or rotated) relative to the treatment planning image 522 in the same plane to improve the alignment (e.g., overlap) between the first patient target region 524 and the first patient target region 526. Furthermore, the first set of patient position-shift vectors may include and/or correspond to instructions as to a first position and/or orientation of the patient for the delivery of therapeutic radiation (e.g., via the positioning and/or orienting of a platform upon which the patient is disposed) such that the first patient target region of the patient may be irradiated more accurately than if the patient is arranged in the position they were in during the acquisition of treatment planning images (e.g., if the platform on which the patient is disposed is in the same position and/or orientation as during the acquisition of the treatment planning images).

Figure 4E:
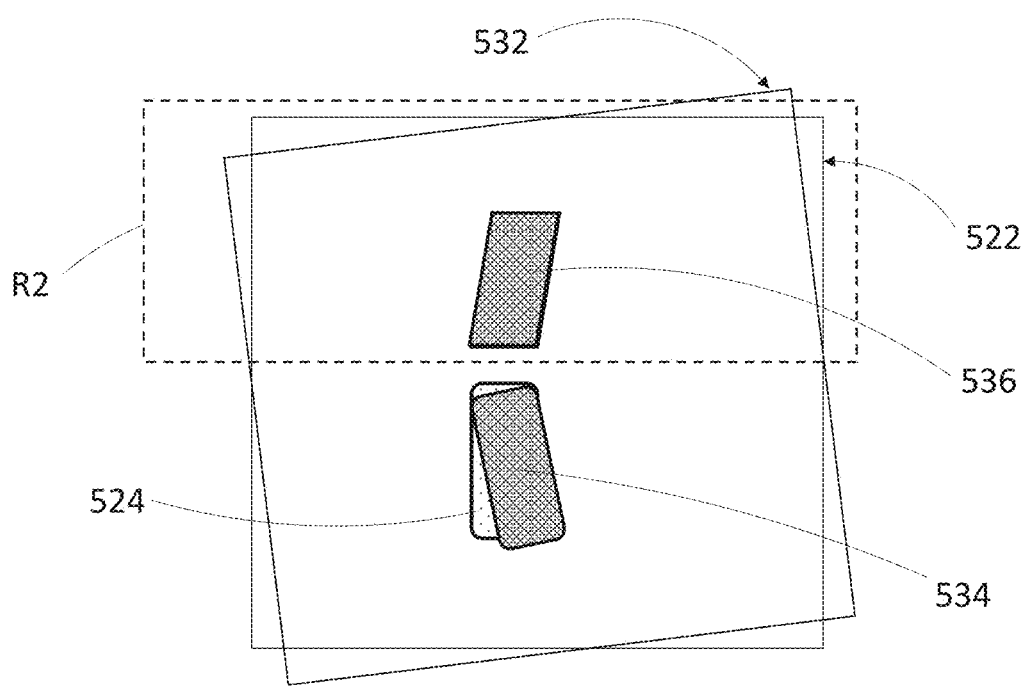

As shown in FIG. 4E, the user may specify a second treatment field R2. Similarly as described above with reference to FIG. 4D, the acquired image 532 may be moved relative to the treatment planning image 522 to align and/or co-located the treatment planning image 522 with the acquired image 532 within in the second treatment field R2. In some embodiments, the second patient target region may be divided into sub-regions (e.g., sub-volumes) that may be represented by voxels, and the coordinates of each voxel of the second patient target region 536 of the acquired image 532 may be compared with the coordinates of a corresponding voxel of the second patient target region 526 in the treatment planning image 522. As shown in FIG. 4E, the acquired image 532 may be rotated counterclockwise relative to the treatment planning image 522 until the treatment planning image 522 and the acquired image 532 are aligned and/or the overlap between the second patient target region 526 and the second patient target region 536 is increased within the second treatment field R2. A second set of patient position-shift vectors may be calculated corresponding to the second treatment field R2 based on locational and/or positional differences between the treatment planning image 522, the acquired image 532 in the second treatment field R2, and the first set of patient position-shift vectors. For example, the second set of patient position-shift vectors may be calculated based on the differences between the treatment planning image 522 and the acquired image 532 prior to the movement of the acquired image 532 to improve the overlap with the treatment planning image 522. In some embodiments, the second set of patient position-shift vectors may reflect the distance and/or direction each voxel of the acquired image 532 is translated to improve the alignment between the second patient target region 536 of the acquired image 532 and the second patient target region 526 of the treatment planning image 522. In some embodiments, the second set of patient position-shift vectors may reflect the distance and/or direction the acquired image 532 may be translated and/or rotated relative to the treatment planning image 522 in the same plane to improve the alignment (e.g., overlap) between the second patient target region 536 and the second patient target region 526. The second set of patient position-shift vectors may be calculated based on the first set of patient position-shift vectors in that, after determining a preliminary set of position shift vectors reflecting the differences between the treatment planning image 522 and the acquired image 532, the second set of patient position-shift vectors may be calculated based on the first position and/or orientation of the patient during irradiation of the first patient target region of the patient. Furthermore, the second set of patient position-shift vectors may include instructions for repositioning and/or reorienting the patient (e.g., via the positioning and/or orienting of a platform upon which the patient is disposed) for the delivery of therapeutic radiation based on the first position/orientation of the patient.

Figure 4F:
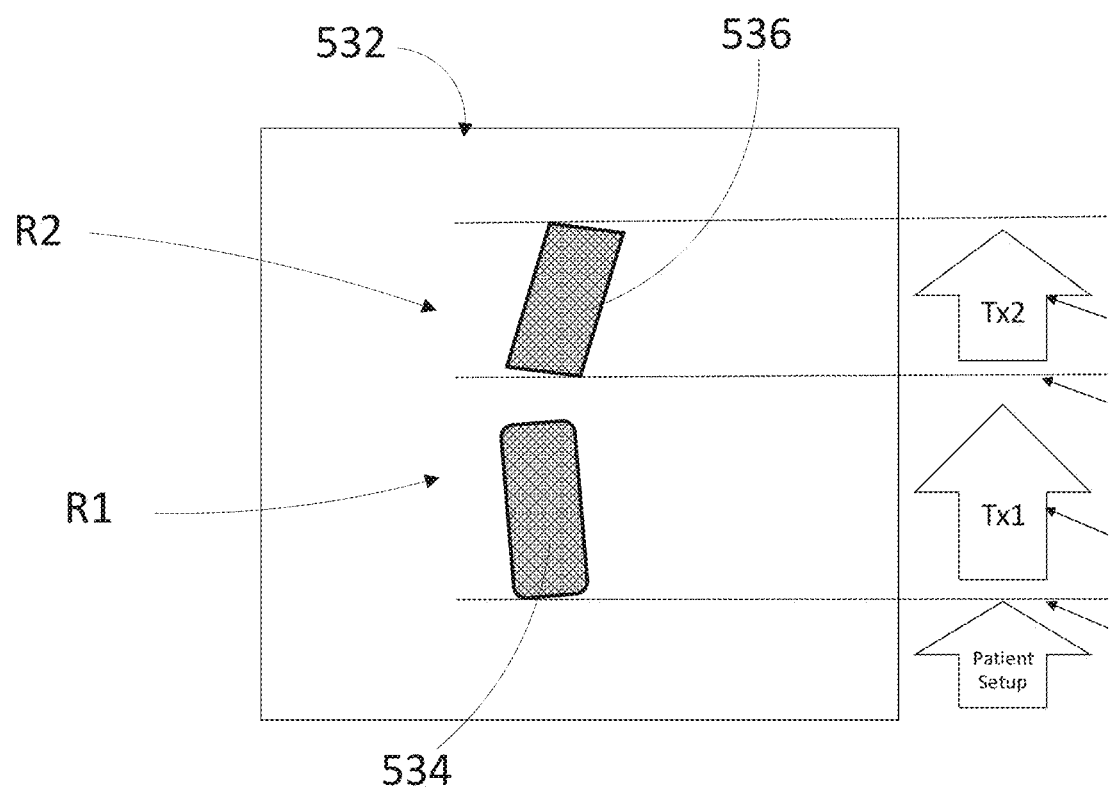

As represented in FIG. 4F, the patient may then be positioned relative to a therapeutic radiation source of a radiation therapy system such that radiation may be applied effectively to the target regions of the patient. For example, the patient may be positioned in a first orientation according to the first set of patient position-shift vectors during patient setup. Therapeutic radiation may then be delivered to the first patient target region while the patient is in the first orientation (e.g., while translating the patient through the radiation therapy system relative to the therapeutic radiation source), as represented by arrow Tx1. For example, a first set of patient platform movements (e.g., beam stations) may correspond to the irradiation of the first patient target region and a second set of patient platform movements (e.g., beam stations) may correspond to the irradiation of the second patient target region. Thus, the platform may move through the first set of patient platform movements (e.g., a first set of patient platform steps or positions) relative to the therapeutic radiation source in the first orientation and with the patient arranged in the first position on the patient platform while the therapeutic radiation is delivered. In some embodiments, rather than the first orientation of the patient being associated with a first set of patient platform movements, the first orientation may be associated with a first set of one or more patient platform steps or positions (e.g., one or more beam stations). For example, the first orientation may be associated with a single first beam station. In some embodiments, the patient platform may move continuously (e.g., along the Y-axis of the patient surface) relative to (e.g., through) a radiation beam path or beam plane of the therapeutic radiation source during delivery of therapeutic radiation to the first patient region while the patient is in the first orientation. Alternatively or additionally, the patient platform may be stepped through a plurality of beam stations and stopped at a beam station during delivery of therapeutic radiation.

After delivering therapeutic radiation to the first patient target region while the patient is in the first orientation, the delivery of therapeutic radiation may be ceased and the patient may be positioned in a second orientation according to the second set of patient position-shift vectors. For example, the patient platform may cease progressing through the system and the user may be notified to adjust the setup position. Next, therapeutic radiation may be delivered to the second patient target region while the patient is in the second orientation (e.g., while translating the patient through the radiation therapy system relative to the therapeutic radiation source), as represented by arrow Tx2, to irradiate the second tumor. For example, the platform may move through a second set of patient platform movements (e.g., a second set of patient platform steps or positions) relative to the therapeutic radiation source in the second orientation and with the patient arranged in the second position orientation on the patient platform while the therapeutic radiation is delivered. In some embodiments, rather than the second orientation of the patient being associated with a second set of patient platform movements, the second orientation may be associated with a second set of one or more patient platform steps or positions (e.g., one or more beam stations, a beam station adjacent to the beam station associated with the first orientation). For example, the second orientation may be associated with a single second beam station. In some embodiments, the patient platform may move continuously (e.g., along the Y-axis of the patient surface) relative to (e.g., through) a radiation beam path or beam plane of the therapeutic radiation source during delivery of therapeutic radiation to the second patient region while the patient is in the second orientation. Alternatively or additionally, the patient platform may be stepped through a plurality of beam stations and stopped at a beam station during delivery of therapeutic radiation.

Systems

As described above, a radiation therapy system, such as any of the radiation therapy systems described herein, may be used to provide image-guided radiation therapy (IGRT) including any of the methods described above. The radiation therapy system may comprise an imaging system comprising any suitable imaging modality, for example, PET, CT, MRI, ultrasound, etc. In some variations, a radiation therapy system may comprise a motion system to which the imaging system may be mounted. Optionally, a therapeutic radiation source and one or more beam-shaping components of the radiation therapy system may be mounted on the same gantry. In some variations, the imaging system may be mounted on a circular gantry configured to rotate around a patient area at a speed of about 30 RPM or more (e.g., about 60 RPM, about 65 RPM, about 70 RPM). Alternatively or additionally, the imaging system may be capable of acquiring tomographic imaging data without any rotation, for example, MRI imaging systems.

A radiation therapy system that may be used to provide IGRT as described above may comprise a therapeutic radiation source that is configured to deliver therapeutic radiation beams in real-time. That is, the therapeutic radiation source may be mounted on a motion system that rapidly moves the radiation source to each firing position around a patient area and the beam-shaping components are configured to change beam-shaping configurations in the time interval between firing positions so that a radiation beam may be applied to a target region before it moves substantially. The greater the latency between image acquisition and radiation delivery, the greater the likelihood that the target region would have moved by the time radiation is delivered. Accordingly, the motion system (e.g., gantry, chassis, arms, etc.) and the beam-shaping components (e.g., jaws, collimators, etc.) may be configured to move (e.g., motion system to move the radiation source to a new firing position) and change configuration (e.g., collimators or jaws to move/change the positioning of the radiopaque elements) in about 10 ms or less. For example, a radiation therapy system may comprise an imaging system (PET, CT, MRI, for example), a rotatable gantry, a linac mounted on the rotatable gantry, and a dynamic multi-leaf collimator mounted on the gantry and disposed in the beam path of the linac. The dynamic multi-leaf collimator may be, for example, a binary multi-leaf collimator, where each leaf is either in an open or closed configuration when located at a firing location, and may be in transit between the open and closed configurations while moving between firing positions. One example of radiation therapy system may have a gantry that rotates at 60 rpm, a dynamic multi-leaf binary collimator may change configuration in 10 ms, and a synchronous therapeutic radiation source may fire several pulses within 10 ms. A synchronous therapeutic radiation source pulses radiation while the leaves of the binary multi-leaf collimator are stationary for a brief period between moving between configurations. The instructions for moving the binary multi-leaf collimator may be generated with a latency as low as 10 ms after the acquisition of the image. Another example of a radiotherapy system may have a gantry that rotates at 5 rpm, a dynamic 2D multi-leaf collimator that is continuously changing configuration, where each leaf may be at any intermediate position between its fully closed and fully open positions when located at a firing position, and asynchronous therapeutic radiation source either pulsing at a rate of about 100 Hz or more or continuously emitting. In some variations, the leaves of the 2D dynamic multi-leaf collimator may be able to move at a velocity that may track twice the velocity of the tumor. The velocity may be based on a geometric calculation using the location of the therapeutic radiation source relative to both the 2D multi-leaf collimator and the target. The latency between the desired 2D multi-leaf collimator leaf position and the corresponding target position may be as low as 10 ms from the acquisition of the image.

The methods and systems described herein may include any suitable patient platform, such as a movable table or couch as described above. For example, the patient platform may comprise any of the patient platforms described in U.S. patent application Ser. No. 15/814,276, filed Nov. 15, 2017, which is hereby incorporated by reference in its entirety.

Rapid Gantry System

Figure 5A:
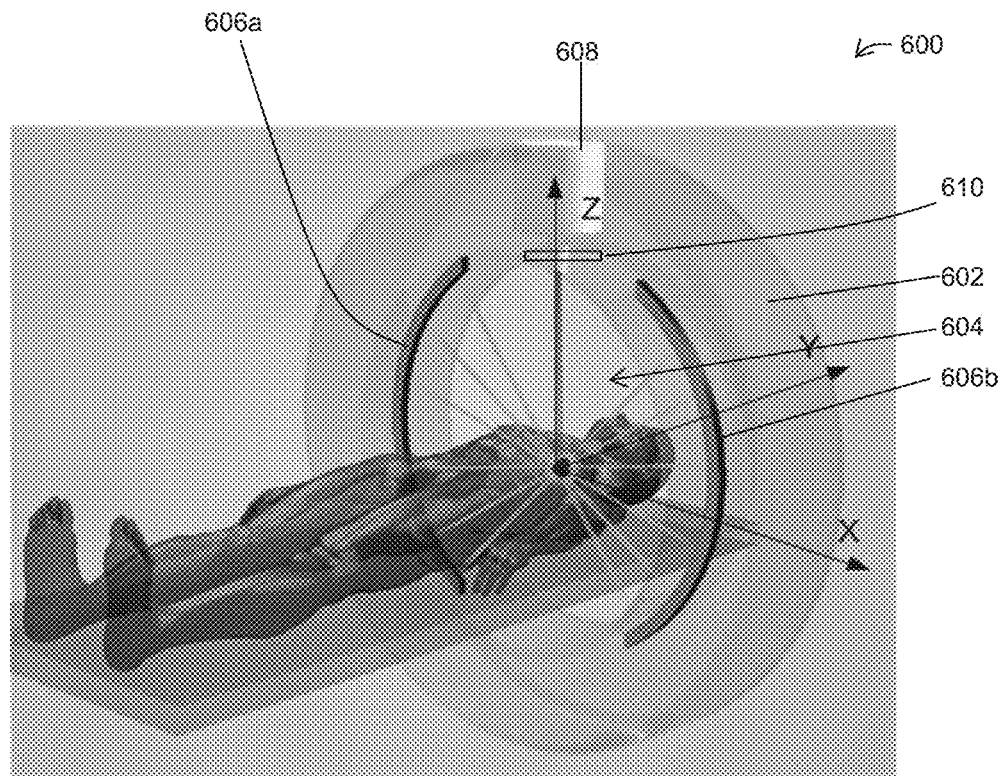
FIG. 5A depicts one variation of a radiation therapy system that may be used with any of the methods described herein.

One variation of a motion system may comprise a rotatable gantry. For example the rotatable gantry may be a continuously rotating gantry, configured to rotate 360 degrees around a patient area. FIG. 5A depicts an example of such a gantry, which may be configured to rotate at a rate of about 60 RPM.

In some variations, a radiotherapy system may rotate a therapeutic radiation source and collimator around an axis, and may optionally stop at various firing angles. A controller for the radiation therapy system may track the speed of the gantry as it rotates about the patient area. The gantry may rotate relatively slowly with a low or fixed angular velocity, or may rotate relatively quickly with a higher angular velocity such that it completes one revolution on the order of the frame rate of the imaging system.

Additional details and variations of a radiation therapy system comprising a high-speed gantry is described in U.S. patent application Ser. No. 15/814,222, filed Nov. 15, 2017, which is hereby incorporated by reference in its entirety.

Dynamic MLC

A radiation therapy system may comprise a beam-shaping component such as an MLC that is configured to change the configuration of the leaves within a selected time interval. For example, the selected time interval may be the time it takes for the motion system to move the linac from a first firing position to a second firing position. The position of the leaf as a function of time may be determined at least in part by the temporal bandwidth and/or configuration transition speed of each MLC leaf. Some radiation therapy systems may comprise a high-speed binary MLC that may comprise leaf-actuation mechanisms that move each of the leaves to a new MLC configuration or pattern on every firing position or gantry angle. This architecture may facilitate generalized target tracking, even of multiple simultaneous targets. Further details of a dynamic binary multi-leaf collimator that may be used in a radiation therapy system are provided in U.S. patent application Ser. No. 15/179,823, filed Jun. 10, 2016, which is hereby incorporated by reference in its entirety.

FIG. 5A depicts one variation of a radiation therapy system that may be used for image-guided radiation therapy implementing any of the methods described herein. The radiation therapy system 600 may comprise a gantry 602 rotatable about a patient area 604, one or more PET detectors 606 mounted on the gantry, a therapeutic radiation source 608 mounted on the gantry, and a dynamic multi-leaf collimator 610 disposed in the beam path of the therapeutic radiation source. In some variations, the radiation therapy system may comprise a first array of PET detectors 606*a* and a second array of PET detectors 606*b* disposed across from the first array, a linear accelerator 608 or linac, and a dynamic binary multi-leaf collimator 610. The system may further comprise a controller that is in communication with the gantry, PET detectors, linac, and MLC, where the controller has one or more memories that may store treatment plans, radiation-firing matrices, fluence maps, system instructions/commands, and a processor configured to execute the calculations and methods described herein. A patient disposed within the patient area may have been injected with a PET tracer that emits positrons, and the PET tracer may accumulate at particular regions of the patient (e.g., irradiation-target regions such as tumor regions). The annihilation of a positron with a nearby electron may result in the emission of two photons traveling in opposite directions to define a line. One or more acquired partial images or detected partial image data may comprise one or more positron annihilation emission paths (i.e., lines of response or LORs, emission paths). In some variations, the PET detectors may be time-of-flight PET detectors, which may help to identify the location of the positron annihilation event. Optionally, radiation therapy system 600 may comprise a CT imaging system mounted on the same gantry as the therapeutic radiation source or mounted on a separate gantry. Additional details and examples of PET-based radiation therapy systems are described in U.S. patent application Ser. No. 15/814,222, filed Nov. 15, 2017 which is hereby incorporated by reference in its entirety.

Figure 5B:
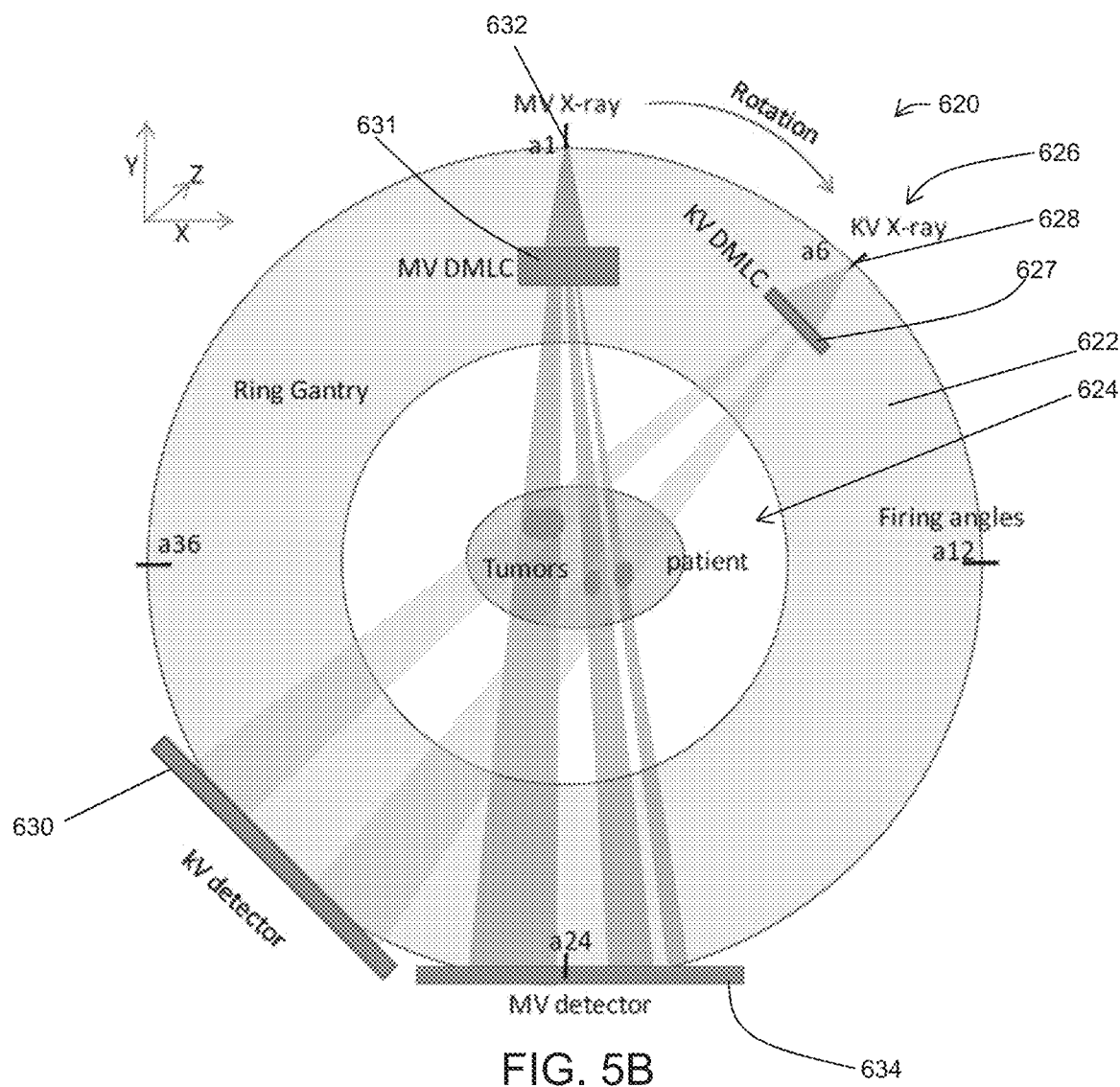
FIG. 5B depicts a cross-sectional view of another variation of a radiation therapy system that may be used with any of the methods described herein.

FIG. 5B depicts another one variation of a radiation therapy system that may be used for image-guided radiation therapy implementing any of the methods described herein. The radiation therapy system 620 may comprise a gantry 622 rotatable about a patient area 624, a kV imaging system 626 having a kV X-ray source 628 and a kV detector 630 mounted on the gantry, and a therapeutic radiation source 632 (e.g., MV X-ray source) and a MV detector 634 mounted on the gantry 622. The kV detector 630 may be located across the kV X-ray source 628 and the MV detector 634 may be located across the MV X-ray source 632. Optionally, the kV imaging system may comprise a dynamic MLC 627 over the kV X-ray source 628. The system may comprise a dynamic MLC 631 disposed over the MV X-ray source 632. Partial images or imaging data may comprise image data acquired by the kV detector after each kV X-ray source pulse. Examples of partial kV X-ray images may include X-ray projection image data, such as 2D projection data. Additional details and examples of PET-based radiation therapy systems are described in PCT/US18/25252, filed Mar. 29, 2018, which is hereby incorporated by reference in its entirety.

Figure 5C:
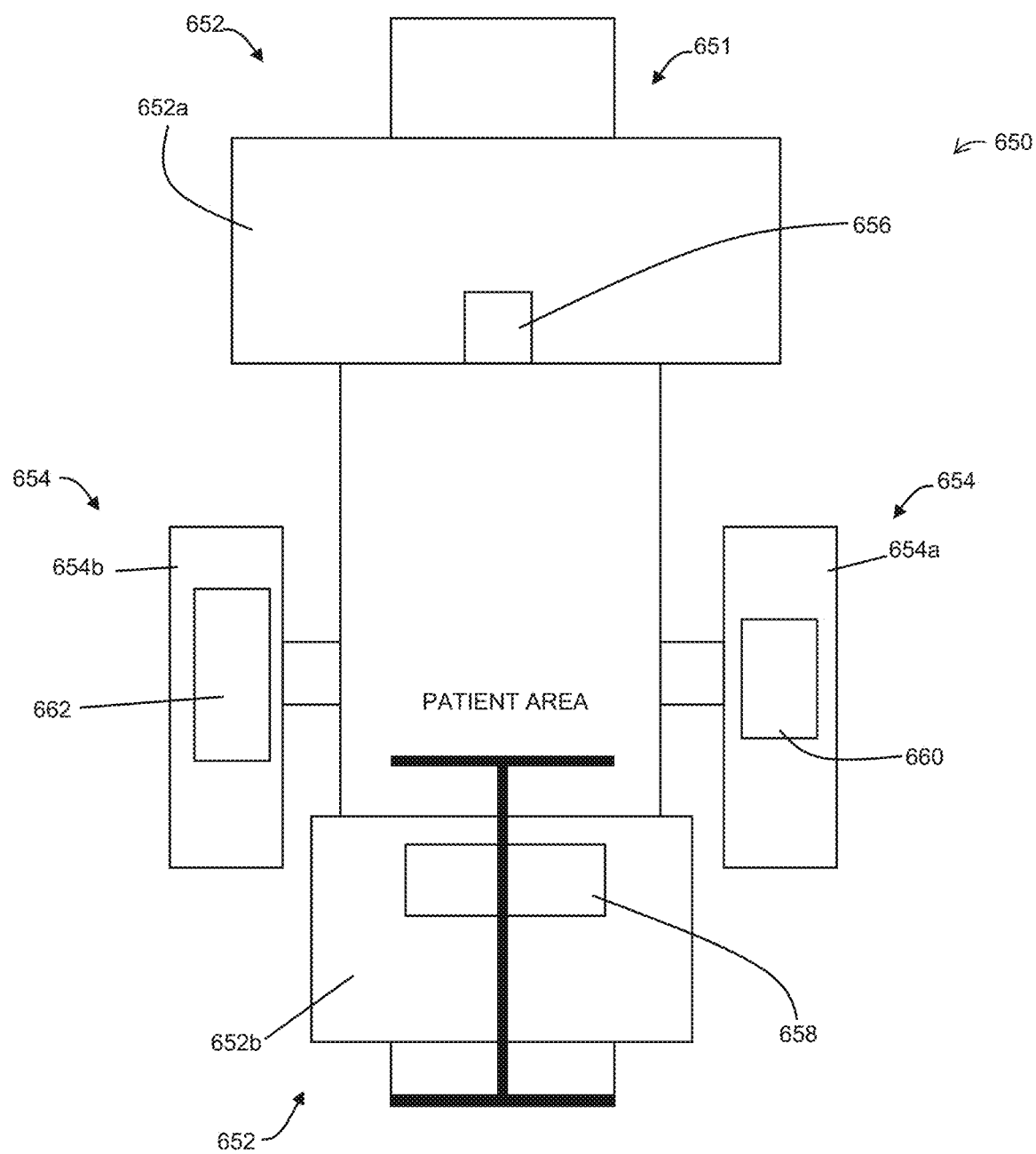
FIG. 5C depicts a schematic representation of another variation of a radiation therapy system that may be used with any of the methods described herein.

FIG. 5C depicts another one variation of a radiation therapy system 650 that may be used for image-guided radiation therapy implementing any of the methods described herein. Radiation therapy system 650 may comprise a gantry 651 comprising a first pair of arms 652 rotatable about a patient area and a second pair of arms 654 rotatable about the patient area, an imaging system comprising a kV radiation source 656 mounted on a first arm 652a of the first pair of arms 652 and a kV detector 658 mounted on a second arm 652b of the first pair of arms 652, and a therapeutic radiation system comprising an MV radiation source 660 mounted on a first arm 654a of the second pair of arms 654 and an MV detector 662 mounted on a second arm 654b of the second pair of arms 654. The first and second arms of the first pair of arms 652 may be located opposite each other (e.g., on opposite sides of the patient area, across from each other, and/or about 180 degrees from each other), such that the kV radiation source 656 and the kV detector 658 are located opposite each other (e.g., the kV detector is located in the beam path of the kV radiation source). The first and second arms of the second pair of arms 654 may be located opposite each other (e.g., on opposite sides of the patient area, across from each other, and/or about 180 degrees from each other), such that the MV radiation source 660 and the MV detector 662 are located opposite each other (e.g., the MV detector is located in the beam path of the MV radiation source). Partial images or imaging data may comprise image data acquired by the kV detector after each kV X-ray source pulse. Examples of partial kV X-ray images may include X-ray projection image data, such as 2D projection data. Additional details and examples of PET-based radiation therapy systems are described in PCT/US18/25252, filed Mar. 29, 2018, which is hereby incorporated by reference in its entirety.

Controller

A system (e.g., a treatment planning system, radiation treatment system) that may be configured to provide patient positioning and/or orientation instructions based on updated patient images may comprise a controller in communication with the imaging system of the radiation therapy system and/or the therapeutic radiation source and/or the multi-leaf collimator and/or gantry. The controller may comprise one or more processors and one or more machine-readable memories in communication with the one or more processors. The controller may be connected to a radiation therapy system and/or other systems by wired or wireless communication channels. In some variations, the controller of a treatment planning system may be located in the same or different room as the patient. For example, the controller may be coupled to a patient platform or disposed on a trolley or medical cart adjacent to the patient and/or operator.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like.

Processor

In some embodiments, a processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), or the like. The processor may be configured to run and/or execute application processes and/or other modules, processes and/or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, or the like.

Memory

In some embodiments, memory may include a database and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor to execute modules, processes and/or functions associated with the system, such as one or more treatment plans, full or high SNR images, partial or low SNR images, the calculation of fluence maps based on treatment plan and/or clinical goals, segmentation of fluence maps into radiation therapy system instructions (e.g., that may direct the operation of the gantry, the patient table, therapeutic radiation source, multi-leaf collimator, and/or any other components of a radiation therapy system and/or diagnostic or treatment planning system), and image and/or data processing associated with treatment planning and/or delivery.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

A user interface may serve as a communication interface between an operator or clinician and the treatment planning system. The user interface may comprise an input device and output device (e.g., touch screen and display) and be configured to receive input data and output data from one or more of the support arm, external magnet, sensor, delivery device, input device, output device, network, database, and server. Sensor data from one or more sensors may be received by user interface and output visually, audibly, and/or through haptic feedback by one or more output devices. As another example, operator control of an input device (e.g., joystick, keyboard, touch screen) may be received by user and then processed by processor and memory for user interface to output a control signal to one or more support arms, external magnets, intracavity devices, and delivery devices. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

Communication

In some embodiments, a treatment planning system and/or radiation therapy system may be in communication with other computing devices via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, apparatuses, and methods described herein may include a radiofrequency receiver, transmitter, and/or optical (e.g., infrared) receiver and transmitter to communicate with one or more devices and/or networks.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein may include various combinations and/or sub-combinations of the functions, components, and/or features of the different embodiments described.

The invention claimed is:

1. A method for positioning a patient for a radiation therapy, the method comprising:
    acquiring an image of a first patient target region and a second patient target region;
    calculating a first set of patient position-shift vectors based on the acquired image and a first treatment planning image of the first patient target region;
    calculating a second set of patient position-shift vectors based on the acquired image, a second treatment planning image of the second patient target region, and the first set of patient position-shift vectors;
    positioning the patient at a first location according to the first set of patient position-shift vectors; and
    positioning the patient at a second location according to the second set of patient position-shift vectors.

2. The method of claim 1, wherein positioning the patient at the first location according to the first set of patient position-shift vectors comprises moving a radiation therapy patient platform and/or a therapeutic radiation source according to the first set of patient position-shift vectors.

3. The method of claim 2, wherein moving the radiation therapy patient platform comprises moving the radiation therapy patient platform along its X-axis, and/or Y-axis, and/or Z-axis.

4. The method of claim 2, wherein moving the radiation therapy patient platform comprises adjusting a yaw and/or a pitch of the radition therapy patient platform and moving the therapeutic radiation source comprises adjusting a roll of a gantry to which the therapeutic radiation source is coupled.

5. The method of claim 1, wherein positioning the patient at the second location according to the second set of patient position-shift vectors comprises moving a radiation therapy patient platform according to the second set of patient position-shift vectors.

6. The method of claim 5, wherein positioning the patient at the second location according to the second set of patient position-shift vectors comprises moving a therapeutic radiation source according to the second set of patient position-shift vectors.

7. The method of claim 6, wherein moving the therapeutic radiation source according to the second set of patient position-shift vectors comprises adjusting a roll of a gantry to which the therapeutic radiation source is coupled.

8. The method of claim 5, wherein moving the radiation therapy patient platform according to the second set of patient position-shift vectors comprises adjusting a yaw and/or a pitch of the radition therapy patient platform.

9. The method of claim 1, wherein the first treatment planning image and the second treatment planning image are the same treatment planning image.

10. The method of claim 1, wherein the acquired image is a PET image.

11. The method of claim 1, wherein the acquired image is a CT image.

12. The method of claim 1, wherein calculating the first set of patient position-shift vectors and the second set of patient position-shift vectors occurs before a therapeutic radiation source is activated.

13. The method of claim 1, further comprising:
calculating a first location difference by comparing a location of the first patient target region in the acquired image with a location of the first patient target region in the first treatment planning image;
calculating a second location difference by comparing a location of the second patient target region in the acquired image with a location of the second patient target region in the second treatment planning image; and
generating a notification if the first location difference or the second location difference exceeds a location difference threshold.

14. The method of claim 1, wherein the first patient target region and the second patient target region comprise one or more tumor regions.

15. The method of claim 14, wherein the first patient target region comprises a first portion of a tumor and the second patient target region comprises a second portion of the tumor.

16. The method of claim 1, wherein the first set of patient position-shift vectors and the second set of patient position-shift vectors comprise distance translations and direction translations.

17. The method of claim 16, wherein the direction translations comprise tilt angles.

18. The method of claim 1, wherein the first location is associated with a first beam station and the second location is associated with a second beam station adjacent to the first beam station.

* * * * *